(12) United States Patent
Pan et al.

(10) Patent No.: US 11,660,328 B2
(45) Date of Patent: May 30, 2023

(54) GLP-2 ANALOGS AND PEPTIBODIES FOR ADMINISTRATION BEFORE, DURING OR AFTER SURGERY

(71) Applicant: TAKEDA PHARMACEUTICAL COMPANY LIMITED, Osaka (JP)

(72) Inventors: Clark Pan, Sudbury, MA (US); Angela Norton, Reading, MA (US); Bettina Strack-Logue, Somerville, MA (US); Clément Olivier, Montreal (CA)

(73) Assignee: TAKEDA PHARMACEUTICAL COMPANY LIMITED, Osaka (JP)

(*) Notice: Subject to any disclaimer, the term of this patent is extended or adjusted under 35 U.S.C. 154(b) by 0 days.

(21) Appl. No.: 16/761,606

(22) PCT Filed: Nov. 5, 2018

(86) PCT No.: PCT/US2018/059175
§ 371 (c)(1),
(2) Date: May 5, 2020

(87) PCT Pub. No.: WO2019/090209
PCT Pub. Date: May 9, 2019

(65) Prior Publication Data
US 2021/0169986 A1 Jun. 10, 2021

Related U.S. Application Data

(60) Provisional application No. 62/582,055, filed on Nov. 6, 2017.

(51) Int. Cl.
*A61K 38/26* (2006.01)
*A61K 47/68* (2017.01)
*A61P 1/00* (2006.01)

(52) U.S. Cl.
CPC .......... *A61K 38/26* (2013.01); *A61K 47/6811* (2017.08); *A61P 1/00* (2018.01)

(58) Field of Classification Search
CPC .............................. C07K 14/605; A61K 47/68
See application file for complete search history.

(56) References Cited

U.S. PATENT DOCUMENTS

| | | | |
|---|---|---|---|
| 7,812,121 B2 | 10/2010 | Baker et al. | |
| 9,060,992 B2* | 6/2015 | Sanguinetti | A61P 1/02 |
| 10,669,323 B2* | 6/2020 | Boettcher | A61P 3/00 |
| 2007/0212355 A1 | 9/2007 | Baker et al. | |
| 2009/0175795 A1 | 7/2009 | Hui | |
| 2010/0113597 A1 | 5/2010 | Oshitani | |
| 2016/0137711 A1 | 5/2016 | Schellenberger et al. | |
| 2017/0020976 A1 | 1/2017 | Sanguinetti et al. | |
| 2017/0362293 A1 | 12/2017 | Sung et al. | |
| 2018/0298077 A1 | 10/2018 | Just et al. | |

FOREIGN PATENT DOCUMENTS

| | | |
|---|---|---|
| EA | 201491934 | 7/2015 |
| JP | 2009510999 | 3/2009 |
| JP | 2010502195 | 1/2010 |
| WO | 2016108654 A1 | 7/2016 |

OTHER PUBLICATIONS

Moore B.A., et al., "GLP-2 receptor agonism ameliorates inflammation and gastrointestinal stasis in murine postoperative ileus," J. Pharmacol. Exp. Ther. May 2010; 333(2):574-83.

Redstone H.A., et al., "The Effect of Glucagon-Like Peptide-2 Receptor Agonists on Colonic AnastomoticWound Healing," Gastroenterology Research and Practice,vol. 2010, Article ID 672453, 12 pages doi:10.1155/2010/672453.

International Search Report and Written Opinion dated Mar. 22, 2019 in connection with PCT/US18/59175.

Kaji T. et al., "Temporal Changes in the Intestinal Growth Promoting Effects of Glucagon-Like Peptide 2 Following Intestinal Resection" Journal of Surgical Research, Academic Press Inc., San Diego, CA, US. Vol. 152, No. 2, Apr. 1, 2009, pp. 271-280.

Thymann T. et al., "Acute Effects of the Glucagon-Like Peptide 2 Analogue, Teduglutide, On Intestinal Adaptation in Newborn Pigs with Short Bowel Syndrome," Journal of Pediatric Gastroenterology and Nutrition, Jan. 1, 2014, p. 1.

Naberhuis J.K. et al., "Teduglutide stimulated intestinal adaptation is complemented by partial enteral nutrition in a neonatal piglet model of short bowel syndrome," Journal of Parenteral and Enteral Nutrition, vol. 41, No. 5, Aug. 24, 2015, pp. 853-865.

Costa B.P. et al., "Effects of teduglutide on histological parameters of intestinal anastomotic healing," European Surgery, Springer Vienna, Vienna, vol. 49, No. 5, Apr. 19, 2017, pp. 218-227.

Office Action dated Sep. 29, 2022 in connection with Japanese Patent Application No. 2020-526107.

Baker A. E., et al., "The dimerization of glucagon-like peptide-2 MIMETIBODY is linked to leucine-17 in the glucagon-like peptide-2 region", Journal of Molecular Recognition, 2012, v. 25, No. 3, p. 155-164.

Redstone H. A., et al., "The effect of glucagon-like Peptide-2 receptor agonists on colonic anastomotic wound healin", Gastroenterol. Res. Pract. 2010, v. 2010, 672453, p. 1-12.

(Continued)

*Primary Examiner* — Gyan Chandra
(74) *Attorney, Agent, or Firm* — Troutman Pepper Hamilton Sanders LLP

(57) ABSTRACT

GLP-2 analogs, such as teduglutide, and fusion proteins of GLP-2 with immunoglobulin are administered before, during or after surgery, particularly resection of the small intestine. When short bowel syndrome develops after surgical resection of the small intestine, parenteral nutrition is usually necessary to compensate for reduced absorption of water and nutrients across the small intestine. GLP-2 analogs and GLP-2 fusion proteins promote growth of small intestine, improve nutrient absorption and can reduce the need for parenteral nutrition after surgery.

8 Claims, 6 Drawing Sheets
Specification includes a Sequence Listing.

(56) References Cited

OTHER PUBLICATIONS

Thymann et al., Acute Effects of the Glucagon-Like Peptide Analogue, Teduglutide, on Intestinal Adaptation in Short Bowel Syndrome. J. Pediatr Gastroenterol Nutr. Jun. 2014:58(6):694-702.†

Costa et al., Teduglutide effects on gene regulation of fibrogenesis on an animal model of intestinal anastomosis. J Surg Res. Aug. 2017:216:87-98.†

Redstone et al., The Effect of Glucagon-Like Peptide-2 Receptor Agonists on Colonic Anastomotic Wound Healing. Gastroenterol Res Pract. 2010:2010:672453.†

Costa et al., Effects of teduglutide on histological parameters of intestinal anastomotic healing. Eur Surg 49,. 218-227 (2017).†

Vegge et al., Glucagon-like peptide-2 induces rapid digestive adaptation following intestinal resection in preterm neonates. Am J Physiol Gastrointest Liver Physiol. Aug. 16, 2013:305(4):G277-85.†

\* cited by examiner
† cited by third party

SEQUENCE LISTING

```
<160> NUMBER OF SEQ ID NOS: 17

<210> SEQ ID NO 1
<211> LENGTH: 33
<212> TYPE: PRT
<213> ORGANISM: Homo sapiens

<400> SEQUENCE: 1

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 2
<211> LENGTH: 264
<212> TYPE: PRT
<213> ORGANISM: Artificial sequence
```

<220> FEATURE:
<223> OTHER INFORMATION: Homo sapiens

<400> SEQUENCE: 2

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Gly Gly Gly Gly Asp Lys Thr His Thr Cys Pro Pro Cys Pro
        35                  40                  45

Ala Pro Glu Ala Ala Gly Gly Pro Ser Val Phe Leu Phe Pro Pro Lys
    50                  55                  60

Pro Lys Asp Thr Leu Met Ile Ser Arg Thr Pro Glu Val Thr Cys Val
65                  70                  75                  80

Val Val Asp Val Ser His Glu Asp Pro Glu Val Lys Phe Asn Trp Tyr
                85                  90                  95

Val Asp Gly Val Glu Val His Asn Ala Lys Thr Lys Pro Arg Glu Glu
            100                 105                 110

Gln Tyr Asn Ser Thr Tyr Arg Val Val Ser Val Leu Thr Val Leu His
        115                 120                 125

Gln Asp Trp Leu Asn Gly Lys Glu Tyr Lys Cys Lys Val Ser Asn Lys
    130                 135                 140

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Asp Glu Leu
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
        195                 200                 205

Tyr Lys Thr Thr Pro Pro Val Leu Asp Ser Asp Gly Ser Phe Phe Leu
    210                 215                 220

Tyr Ser Lys Leu Thr Val Asp Lys Ser Arg Trp Gln Gln Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Pro Gly
            260

<210> SEQ ID NO 3
<211> LENGTH: 265
<212> TYPE: PRT
<213> ORGANISM: Artificial sequence
<220> FEATURE:
<223> OTHER INFORMATION: Homo sapiens

<400> SEQUENCE: 3

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Gly Gly Gly Gly Asp Lys Thr His Thr Cys Pro Pro Cys Pro
        35                  40                  45

Ala Pro Glu Ala Ala Gly Gly Pro Ser Val Phe Leu Phe Pro Pro Lys
    50                  55                  60

Pro Lys Asp Thr Leu Met Ile Ser Arg Thr Pro Glu Val Thr Cys Val

```
                65                  70                  75                  80
        Val Val Asp Val Ser His Glu Asp Pro Glu Val Lys Phe Asn Trp Tyr
                            85                  90                  95

Val Asp Gly Val Glu Val His Asn Ala Lys Thr Lys Pro Arg Glu Glu
                            100                 105                 110

Gln Tyr Asn Ser Thr Tyr Arg Val Val Ser Val Leu Thr Val Leu His
                            115                 120                 125

Gln Asp Trp Leu Asn Gly Lys Glu Tyr Lys Cys Lys Val Ser Asn Lys
                    130                 135                 140

Ala Leu Pro Ala Pro Ile Glu Lys Thr Ile Ser Lys Ala Lys Gly Gln
        145                 150                 155                 160

Pro Arg Glu Pro Gln Val Tyr Thr Leu Pro Pro Ser Arg Asp Glu Leu
                            165                 170                 175

Thr Lys Asn Gln Val Ser Leu Thr Cys Leu Val Lys Gly Phe Tyr Pro
                            180                 185                 190

Ser Asp Ile Ala Val Glu Trp Glu Ser Asn Gly Gln Pro Glu Asn Asn
                    195                 200                 205

Tyr Lys Thr Thr Pro Pro Val Leu Asp Ser Asp Gly Ser Phe Phe Leu
                    210                 215                 220

Tyr Ser Lys Leu Thr Val Asp Lys Ser Arg Trp Gln Gln Gly Asn Val
        225                 230                 235                 240

Phe Ser Cys Ser Val Met His Glu Ala Leu His Asn His Tyr Thr Gln
                            245                 250                 255

Lys Ser Leu Ser Leu Ser Pro Gly Lys
                    260                 265

<210> SEQ ID NO 4
<211> LENGTH: 274
<212> TYPE: PRT
<213> ORGANISM: Homo sapiens

<400> SEQUENCE: 4

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
                    20                  25                  30

Asp Gly Gly Gly Gly Ser Gly Gly Gly Gly Ser Gly Gly Gly Gly Ser
                35                  40                  45

Asp Lys Thr His Thr Cys Pro Pro Cys Pro Ala Pro Glu Ala Ala Gly
        50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser His
                    85                  90                  95

Glu Asp Pro Glu Val Lys Phe Asn Trp Tyr Val Asp Gly Val Glu Val
                    100                 105                 110

His Asn Ala Lys Thr Lys Pro Arg Glu Glu Gln Tyr Asn Ser Thr Tyr
                115                 120                 125

Arg Val Val Ser Val Leu Thr Val Leu His Gln Asp Trp Leu Asn Gly
            130                 135                 140

Lys Glu Tyr Lys Cys Lys Val Ser Asn Lys Ala Leu Pro Ala Pro Ile
145                 150                 155                 160

Glu Lys Thr Ile Ser Lys Ala Lys Gly Gln Pro Arg Glu Pro Gln Val
                    165                 170                 175
```

Tyr Thr Leu Pro Pro Ser Arg Asp Glu Leu Thr Lys Asn Gln Val Ser
            180                 185                 190

Leu Thr Cys Leu Val Lys Gly Phe Tyr Pro Ser Asp Ile Ala Val Glu
        195                 200                 205

Trp Glu Ser Asn Gly Gln Pro Glu Asn Asn Tyr Lys Thr Thr Pro Pro
    210                 215                 220

Val Leu Asp Ser Asp Gly Ser Phe Phe Leu Tyr Ser Lys Leu Thr Val
225                 230                 235                 240

Asp Lys Ser Arg Trp Gln Gln Gly Asn Val Phe Ser Cys Ser Val Met
                245                 250                 255

His Glu Ala Leu His Asn His Tyr Thr Gln Lys Ser Leu Ser Leu Ser
            260                 265                 270

Pro Gly

<210> SEQ ID NO 5
<211> LENGTH: 275
<212> TYPE: PRT
<213> ORGANISM: Artificial sequence
<220> FEATURE:
<223> OTHER INFORMATION: Homo sapiens

<400> SEQUENCE: 5

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Gly Gly Gly Ser Gly Gly Gly Ser Gly Gly Gly Gly Ser
        35                  40                  45

Asp Lys Thr His Thr Cys Pro Pro Cys Pro Ala Pro Glu Ala Ala Gly
    50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser His
                85                  90                  95

Glu Asp Pro Glu Val Lys Phe Asn Trp Tyr Val Asp Gly Val Glu Val
            100                 105                 110

His Asn Ala Lys Thr Lys Pro Arg Glu Glu Gln Tyr Asn Ser Thr Tyr
        115                 120                 125

Arg Val Val Ser Val Leu Thr Val Leu His Gln Asp Trp Leu Asn Gly
    130                 135                 140

Lys Glu Tyr Lys Cys Lys Val Ser Asn Lys Ala Leu Pro Ala Pro Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Arg Asp Glu Leu Thr Lys Asn Gln Val Ser
            180                 185                 190

Leu Thr Cys Leu Val Lys Gly Phe Tyr Pro Ser Asp Ile Ala Val Glu
        195                 200                 205

Trp Glu Ser Asn Gly Gln Pro Glu Asn Asn Tyr Lys Thr Thr Pro Pro
    210                 215                 220

Val Leu Asp Ser Asp Gly Ser Phe Phe Leu Tyr Ser Lys Leu Thr Val
225                 230                 235                 240

Asp Lys Ser Arg Trp Gln Gln Gly Asn Val Phe Ser Cys Ser Val Met
                245                 250                 255

His Glu Ala Leu His Asn His Tyr Thr Gln Lys Ser Leu Ser Leu Ser

```
              260                 265                 270

Pro Gly Lys
        275

<210> SEQ ID NO 6
<211> LENGTH: 259
<212> TYPE: PRT
<213> ORGANISM: Artificial sequence
<220> FEATURE:
<223> OTHER INFORMATION: Homo sapiens

<400> SEQUENCE: 6

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Asp Lys Thr His Thr Cys Pro Cys Pro Ala Pro Glu Ala Ala
        35                  40                  45

Gly Gly Pro Ser Val Phe Leu Phe Pro Pro Lys Pro Lys Asp Thr Leu
50                  55                  60

Met Ile Ser Arg Thr Pro Glu Val Thr Cys Val Val Val Asp Val Ser
65                  70                  75                  80

His Glu Asp Pro Glu Val Lys Phe Asn Trp Tyr Val Asp Gly Val Glu
                85                  90                  95

Val His Asn Ala Lys Thr Lys Pro Arg Glu Glu Gln Tyr Asn Ser Thr
            100                 105                 110

Tyr Arg Val Val Ser Val Leu Thr Val Leu His Gln Asp Trp Leu Asn
        115                 120                 125

Gly Lys Glu Tyr Lys Cys Lys Val Ser Asn Lys Ala Leu Pro Ala Pro
    130                 135                 140

Ile Glu Lys Thr Ile Ser Lys Ala Lys Gly Gln Pro Arg Glu Pro Gln
145                 150                 155                 160

Val Tyr Thr Leu Pro Pro Ser Arg Asp Glu Leu Thr Lys Asn Gln Val
                165                 170                 175

Ser Leu Thr Cys Leu Val Lys Gly Phe Tyr Pro Ser Asp Ile Ala Val
            180                 185                 190

Glu Trp Glu Ser Asn Gly Gln Pro Glu Asn Asn Tyr Lys Thr Thr Pro
        195                 200                 205

Pro Val Leu Asp Ser Asp Gly Ser Phe Phe Leu Tyr Ser Lys Leu Thr
    210                 215                 220

Val Asp Lys Ser Arg Trp Gln Gln Gly Asn Val Phe Ser Cys Ser Val
225                 230                 235                 240

Met His Glu Ala Leu His Asn His Tyr Thr Gln Lys Ser Leu Ser Leu
                245                 250                 255

Ser Pro Gly

<210> SEQ ID NO 7
<211> LENGTH: 276
<212> TYPE: PRT
<213> ORGANISM: Artificial sequence
<220> FEATURE:
<223> OTHER INFORMATION: Homo sapiens

<400> SEQUENCE: 7

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
```

```
            20                  25                  30
Asp Gly Gly Gly Gly Gly Ser Gly Gly Gly Ser Gly Gly Gly
        35                  40                  45
Gly Ser Asp Lys Thr His Thr Cys Pro Pro Cys Pro Ala Pro Glu Ala
 50                  55                  60
Ala Gly Gly Pro Ser Val Phe Leu Phe Pro Pro Lys Pro Lys Asp Thr
 65                  70                  75                  80
Leu Met Ile Ser Arg Thr Pro Glu Val Thr Cys Val Val Val Asp Val
                 85                  90                  95
Ser His Glu Asp Pro Glu Val Lys Phe Asn Trp Tyr Val Asp Gly Val
                100                 105                 110
Glu Val His Asn Ala Lys Thr Lys Pro Arg Glu Glu Gln Tyr Asn Ser
            115                 120                 125
Thr Tyr Arg Val Val Ser Val Leu Thr Val Leu His Gln Asp Trp Leu
        130                 135                 140
Asn Gly Lys Glu Tyr Lys Cys Lys Val Ser Asn Lys Ala Leu Pro Ala
145                 150                 155                 160
Pro Ile Glu Lys Thr Ile Ser Lys Ala Lys Gly Gln Pro Arg Glu Pro
                165                 170                 175
Gln Val Tyr Thr Leu Pro Pro Ser Arg Asp Glu Leu Thr Lys Asn Gln
            180                 185                 190
Val Ser Leu Thr Cys Leu Val Lys Gly Phe Tyr Pro Ser Asp Ile Ala
        195                 200                 205
Val Glu Trp Glu Ser Asn Gly Gln Pro Glu Asn Asn Tyr Lys Thr Thr
    210                 215                 220
Pro Pro Val Leu Asp Ser Asp Gly Ser Phe Phe Leu Tyr Ser Lys Leu
225                 230                 235                 240
Thr Val Asp Lys Ser Arg Trp Gln Gln Gly Asn Val Phe Ser Cys Ser
                245                 250                 255
Val Met His Glu Ala Leu His Asn His Tyr Thr Gln Lys Ser Leu Ser
            260                 265                 270
Leu Ser Pro Gly
        275

<210> SEQ ID NO 8
<211> LENGTH: 316
<212> TYPE: PRT
<213> ORGANISM: Artificial sequence
<220> FEATURE:
<223> OTHER INFORMATION: Homo sapiens

<400> SEQUENCE: 8

His Gly Asp Gly Ser Phe Ser Asp Glu Met Asn Thr Ile Leu Asp Asn
 1               5                  10                  15
Leu Ala Ala Arg Asp Phe Ile Asn Trp Leu Ile Gln Thr Lys Ile Thr
             20                  25                  30
Asp Gly Ala Pro Gly Gly Gly Gly Ala Ala Ala Ala Gly Gly
        35                  40                  45
Gly Gly Gly Gly Ala Pro Gly Gly Gly Ala Ala Ala Ala
 50                  55                  60
Gly Gly Gly Gly Gly Ala Pro Gly Gly Gly Ala Ala Ala
 65                  70                  75                  80
Ala Ala Gly Gly Gly Gly Gly Ala Pro Asp Lys Thr His Thr Cys
                 85                  90                  95
Pro Pro Cys Pro Ala Pro Glu Ala Ala Gly Gly Pro Ser Val Phe Leu
```

```
            100                 105                 110
Phe Pro Pro Lys Pro Lys Asp Thr Leu Met Ile Ser Arg Thr Pro Glu
        115                 120                 125

Val Thr Cys Val Val Val Asp Val Ser His Glu Asp Pro Glu Val Lys
    130                 135                 140

Phe Asn Trp Tyr Val Asp Gly Val Glu Val His Asn Ala Lys Thr Lys
145                 150                 155                 160

Pro Arg Glu Glu Gln Tyr Asn Ser Thr Tyr Arg Val Val Ser Val Leu
            165                 170                 175

Thr Val Leu His Gln Asp Trp Leu Asn Gly Lys Glu Tyr Lys Cys Lys
        180                 185                 190

Val Ser Asn Lys Ala Leu Pro Ala Pro Ile Glu Lys Thr Ile Ser Lys
    195                 200                 205

Ala Lys Gly Gln Pro Arg Glu Pro Gln Val Tyr Thr Leu Pro Pro Ser
210                 215                 220

Arg Asp Glu Leu Thr Lys Asn Gln Val Ser Leu Thr Cys Leu Val Lys
225                 230                 235                 240

Gly Phe Tyr Pro Ser Asp Ile Ala Val Glu Trp Glu Ser Asn Gly Gln
            245                 250                 255

Pro Glu Asn Asn Tyr Lys Thr Thr Pro Pro Val Leu Asp Ser Asp Gly
        260                 265                 270

Ser Phe Phe Leu Tyr Ser Lys Leu Thr Val Asp Lys Ser Arg Trp Gln
    275                 280                 285

Gln Gly Asn Val Phe Ser Cys Ser Val Met His Glu Ala Leu His Asn
290                 295                 300

His Tyr Thr Gln Lys Ser Leu Ser Leu Ser Pro Gly
305                 310                 315

<210> SEQ ID NO 9
<211> LENGTH: 266
<212> TYPE: PRT
<213> ORGANISM: Artificial sequence
<220> FEATURE:
<223> OTHER INFORMATION: Homo sapiens

<400> SEQUENCE: 9

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Gly Gly Gly Gly Gly Gly Asp Lys Thr His Thr Cys Pro Pro
        35                  40                  45

Cys Pro Ala Pro Glu Ala Ala Gly Gly Pro Ser Val Phe Leu Phe Pro
    50                  55                  60

Pro Lys Pro Lys Asp Thr Leu Met Ile Ser Arg Thr Pro Glu Val Thr
65                  70                  75                  80

Cys Val Val Val Asp Val Ser His Glu Asp Pro Glu Val Lys Phe Asn
            85                  90                  95

Trp Tyr Val Asp Gly Val Glu Val His Asn Ala Lys Thr Lys Pro Arg
            100                 105                 110

Glu Glu Gln Tyr Asn Ser Thr Tyr Arg Val Val Ser Val Leu Thr Val
        115                 120                 125

Leu His Gln Asp Trp Leu Asn Gly Lys Glu Tyr Lys Cys Lys Val Ser
    130                 135                 140

Asn Lys Ala Leu Pro Ala Pro Ile Glu Lys Thr Ile Ser Lys Ala Lys
```

```
145                 150                 155                 160
Gly Gln Pro Arg Glu Pro Gln Val Tyr Thr Leu Pro Pro Ser Arg Asp
                165                 170                 175
Glu Leu Thr Lys Asn Gln Val Ser Leu Thr Cys Leu Val Lys Gly Phe
            180                 185                 190
Tyr Pro Ser Asp Ile Ala Val Glu Trp Glu Ser Asn Gly Gln Pro Glu
        195                 200                 205
Asn Asn Tyr Lys Thr Thr Pro Val Leu Asp Ser Asp Gly Ser Phe
    210                 215                 220
Phe Leu Tyr Ser Lys Leu Thr Val Asp Lys Ser Arg Trp Gln Gln Gly
225                 230                 235                 240
Asn Val Phe Ser Cys Ser Val Met His Glu Ala Leu His Asn His Tyr
                245                 250                 255
Thr Gln Lys Ser Leu Ser Leu Ser Pro Gly
            260                 265

<210> SEQ ID NO 10
<211> LENGTH: 269
<212> TYPE: PRT
<213> ORGANISM: Artificial sequence
<220> FEATURE:
<223> OTHER INFORMATION: Homo sapiens

<400> SEQUENCE: 10

His Gly Asp Gly Ser Phe Ser Asp Glu Met Asn Thr Ile Leu Asp Asn
1               5                   10                  15
Leu Ala Ala Arg Asp Phe Ile Asn Trp Leu Ile Gln Thr Lys Ile Thr
                20                  25                  30
Asp Gly Gly Gly Ser Gly Gly Gly Ser Asp Lys Thr His Thr
            35                  40                  45
Cys Pro Pro Cys Pro Ala Pro Glu Ala Ala Gly Gly Pro Ser Val Phe
        50                  55                  60
Leu Phe Pro Pro Lys Pro Lys Asp Thr Leu Met Ile Ser Arg Thr Pro
65                  70                  75                  80
Glu Val Thr Cys Val Val Val Asp Val Ser His Glu Asp Pro Glu Val
                85                  90                  95
Lys Phe Asn Trp Tyr Val Asp Gly Val Glu Val His Asn Ala Lys Thr
                100                 105                 110
Lys Pro Arg Glu Glu Gln Tyr Asn Ser Thr Tyr Arg Val Val Ser Val
            115                 120                 125
Leu Thr Val Leu His Gln Asp Trp Leu Asn Gly Lys Glu Tyr Lys Cys
        130                 135                 140
Lys Val Ser Asn Lys Ala Leu Pro Ala Pro Ile Glu Lys Thr Ile Ser
145                 150                 155                 160
Lys Ala Lys Gly Gln Pro Arg Glu Pro Gln Val Tyr Thr Leu Pro Pro
                165                 170                 175
Ser Arg Asp Glu Leu Thr Lys Asn Gln Val Ser Leu Thr Cys Leu Val
            180                 185                 190
Lys Gly Phe Tyr Pro Ser Asp Ile Ala Val Glu Trp Glu Ser Asn Gly
        195                 200                 205
Gln Pro Glu Asn Asn Tyr Lys Thr Thr Pro Val Leu Asp Ser Asp
    210                 215                 220
Gly Ser Phe Phe Leu Tyr Ser Lys Leu Thr Val Asp Lys Ser Arg Trp
225                 230                 235                 240
Gln Gln Gly Asn Val Phe Ser Cys Ser Val Met His Glu Ala Leu His
```

```
                        245                 250                 255
Asn His Tyr Thr Gln Lys Ser Leu Ser Leu Ser Pro Gly
                260                 265

<210> SEQ ID NO 11
<211> LENGTH: 635
<212> TYPE: PRT
<213> ORGANISM: Artificial sequence
<220> FEATURE:
<223> OTHER INFORMATION: Homo sapiens

<400> SEQUENCE: 11

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Gly Gly Gly Gly Gly Ser Gly Gly Gly Ser Gly Gly Gly
        35                  40                  45

Gly Ser Asp Ala His Lys Ser Glu Val Ala His Arg Phe Lys Asp Leu
65              55                  60

Gly Glu Glu Asn Phe Lys Ala Leu Val Leu Ile Ala Phe Ala Gln Tyr
65              70                  75                  80

Leu Gln Gln Cys Pro Phe Glu Asp His Val Lys Leu Val Asn Glu Val
            85                  90                  95

Thr Glu Phe Ala Lys Thr Cys Val Ala Asp Glu Ser Ala Glu Asn Cys
        100                 105                 110

Asp Lys Ser Leu His Thr Leu Phe Gly Asp Lys Leu Cys Thr Val Ala
    115                 120                 125

Thr Leu Arg Glu Thr Tyr Gly Glu Met Ala Asp Cys Cys Ala Lys Gln
130                 135                 140

Glu Pro Glu Arg Asn Glu Cys Phe Leu Gln His Lys Asp Asp Asn Pro
145                 150                 155                 160

Asn Leu Pro Arg Leu Val Arg Pro Glu Val Asp Val Met Cys Thr Ala
                165                 170                 175

Phe His Asp Asn Glu Glu Thr Phe Leu Lys Lys Tyr Leu Tyr Glu Ile
            180                 185                 190

Ala Arg Arg His Pro Tyr Phe Tyr Ala Pro Glu Leu Leu Phe Phe Ala
        195                 200                 205

Lys Arg Tyr Lys Ala Ala Phe Thr Glu Cys Cys Gln Ala Ala Asp Lys
    210                 215                 220

Ala Ala Cys Leu Leu Pro Lys Leu Asp Glu Leu Arg Asp Glu Gly Lys
225                 230                 235                 240

Ala Ser Ser Ala Lys Gln Arg Leu Lys Cys Ala Ser Leu Gln Lys Phe
                245                 250                 255

Gly Glu Arg Ala Phe Lys Ala Trp Ala Val Ala Arg Leu Ser Gln Arg
            260                 265                 270

Phe Pro Lys Ala Glu Phe Ala Glu Val Ser Lys Leu Val Thr Asp Leu
        275                 280                 285

Thr Lys Val His Thr Glu Cys Cys His Gly Asp Leu Leu Glu Cys Ala
    290                 295                 300

Asp Asp Arg Ala Asp Leu Ala Lys Tyr Ile Cys Glu Asn Gln Asp Ser
305                 310                 315                 320

Ile Ser Ser Lys Leu Lys Glu Cys Cys Glu Lys Pro Leu Leu Glu Lys
                325                 330                 335

Ser His Cys Ile Ala Glu Val Glu Asn Asp Glu Met Pro Ala Asp Leu
```

-continued

```
                340                 345                 350
Pro Ser Leu Ala Ala Asp Phe Val Glu Ser Lys Asp Val Cys Lys Asn
            355                 360                 365

Tyr Ala Glu Ala Lys Asp Val Phe Leu Gly Met Phe Leu Tyr Glu Tyr
        370                 375                 380

Ala Arg Arg His Pro Asp Tyr Ser Val Val Leu Leu Leu Arg Leu Ala
385                 390                 395                 400

Lys Thr Tyr Lys Thr Thr Leu Glu Lys Cys Cys Ala Ala Ala Asp Pro
                405                 410                 415

His Glu Cys Tyr Ala Lys Val Phe Asp Glu Phe Lys Pro Leu Val Glu
            420                 425                 430

Glu Pro Gln Asn Leu Ile Lys Gln Asn Cys Glu Leu Phe Glu Gln Leu
        435                 440                 445

Gly Glu Tyr Lys Phe Gln Asn Ala Leu Leu Val Arg Tyr Thr Lys Lys
    450                 455                 460

Val Pro Gln Val Ser Thr Pro Thr Leu Val Glu Val Ser Arg Asn Leu
465                 470                 475                 480

Gly Lys Val Gly Ser Lys Cys Cys Lys His Pro Glu Ala Lys Arg Met
                485                 490                 495

Pro Cys Ala Glu Asp Tyr Leu Ser Val Val Leu Asn Gln Leu Cys Val
            500                 505                 510

Leu His Glu Lys Thr Pro Val Ser Asp Arg Val Thr Lys Cys Cys Thr
        515                 520                 525

Glu Ser Leu Val Asn Arg Arg Pro Cys Phe Ser Ala Leu Glu Val Asp
    530                 535                 540

Glu Thr Tyr Val Pro Lys Glu Phe Asn Ala Glu Thr Phe Thr Phe His
545                 550                 555                 560

Ala Asp Ile Cys Thr Leu Ser Glu Lys Glu Arg Gln Ile Lys Lys Gln
                565                 570                 575

Thr Ala Leu Val Glu Leu Val Lys His Lys Pro Lys Ala Thr Lys Glu
            580                 585                 590

Gln Leu Lys Ala Val Met Asp Asp Phe Ala Ala Phe Val Glu Lys Cys
        595                 600                 605

Cys Lys Ala Asp Asp Lys Glu Thr Cys Phe Ala Glu Glu Gly Lys Lys
    610                 615                 620

Leu Val Ala Ala Ser Arg Ala Ala Leu Gly Leu
625                 630                 635
```

<210> SEQ ID NO 12
<211> LENGTH: 651
<212> TYPE: PRT
<213> ORGANISM: Artificial sequence
<220> FEATURE:
<223> OTHER INFORMATION: Homo sapiens

<400> SEQUENCE: 12

```
His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp His Gly Asp Gly Ser Phe Ser Asp Glu Met Asn Thr Ile Leu Asp
        35                  40                  45

Asn Leu Ala Ala Arg Asp Phe Ile Asn Trp Leu Ile Gln Thr Lys Ile
    50                  55                  60

Thr Asp Asp Ala His Lys Ser Glu Val Ala His Arg Phe Lys Asp Leu
```

```
                65                  70                  75                  80
Gly Glu Glu Asn Phe Lys Ala Leu Val Leu Ile Ala Phe Ala Gln Tyr
                    85                  90                  95

Leu Gln Gln Cys Pro Phe Glu Asp His Val Lys Leu Val Asn Glu Val
                100                 105                 110

Thr Glu Phe Ala Lys Thr Cys Val Ala Asp Glu Ser Ala Glu Asn Cys
                115                 120                 125

Asp Lys Ser Leu His Thr Leu Phe Gly Asp Lys Leu Cys Thr Val Ala
        130                 135                 140

Thr Leu Arg Glu Thr Tyr Gly Glu Met Ala Asp Cys Cys Ala Lys Gln
145                 150                 155                 160

Glu Pro Glu Arg Asn Glu Cys Phe Leu Gln His Lys Asp Asp Asn Pro
                    165                 170                 175

Asn Leu Pro Arg Leu Val Arg Pro Glu Val Asp Val Met Cys Thr Ala
                180                 185                 190

Phe His Asp Asn Glu Glu Thr Phe Leu Lys Lys Tyr Leu Tyr Glu Ile
        195                 200                 205

Ala Arg Arg His Pro Tyr Phe Tyr Ala Pro Glu Leu Leu Phe Phe Ala
    210                 215                 220

Lys Arg Tyr Lys Ala Ala Phe Thr Glu Cys Cys Gln Ala Ala Asp Lys
225                 230                 235                 240

Ala Ala Cys Leu Leu Pro Lys Leu Asp Glu Leu Arg Asp Glu Gly Lys
                    245                 250                 255

Ala Ser Ser Ala Lys Gln Arg Leu Lys Cys Ala Ser Leu Gln Lys Phe
                260                 265                 270

Gly Glu Arg Ala Phe Lys Ala Trp Ala Val Ala Arg Leu Ser Gln Arg
        275                 280                 285

Phe Pro Lys Ala Glu Phe Ala Glu Val Ser Lys Leu Val Thr Asp Leu
    290                 295                 300

Thr Lys Val His Thr Glu Cys Cys His Gly Asp Leu Leu Glu Cys Ala
305                 310                 315                 320

Asp Asp Arg Ala Asp Leu Ala Lys Tyr Ile Cys Glu Asn Gln Asp Ser
                    325                 330                 335

Ile Ser Ser Lys Leu Lys Glu Cys Cys Glu Lys Pro Leu Leu Glu Lys
                340                 345                 350

Ser His Cys Ile Ala Glu Val Glu Asn Asp Glu Met Pro Ala Asp Leu
        355                 360                 365

Pro Ser Leu Ala Ala Asp Phe Val Glu Ser Lys Asp Val Cys Lys Asn
    370                 375                 380

Tyr Ala Glu Ala Lys Asp Val Phe Leu Gly Met Phe Leu Tyr Glu Tyr
385                 390                 395                 400

Ala Arg Arg His Pro Asp Tyr Ser Val Val Leu Leu Leu Arg Leu Ala
                    405                 410                 415

Lys Thr Tyr Lys Thr Thr Leu Glu Lys Cys Cys Ala Ala Ala Asp Pro
                420                 425                 430

His Glu Cys Tyr Ala Lys Val Phe Asp Glu Phe Lys Pro Leu Val Glu
        435                 440                 445

Glu Pro Gln Asn Leu Ile Lys Gln Asn Cys Glu Leu Phe Glu Gln Leu
    450                 455                 460

Gly Glu Tyr Lys Phe Gln Asn Ala Leu Leu Val Arg Tyr Thr Lys Lys
465                 470                 475                 480

Val Pro Gln Val Ser Thr Pro Thr Leu Val Glu Val Ser Arg Asn Leu
                    485                 490                 495
```

```
Gly Lys Val Gly Ser Lys Cys Cys Lys His Pro Glu Ala Lys Arg Met
            500                 505                 510

Pro Cys Ala Glu Asp Tyr Leu Ser Val Val Leu Asn Gln Leu Cys Val
            515                 520                 525

Leu His Glu Lys Thr Pro Val Ser Asp Arg Val Thr Lys Cys Cys Thr
            530                 535                 540

Glu Ser Leu Val Asn Arg Arg Pro Cys Phe Ser Ala Leu Glu Val Asp
545                 550                 555                 560

Glu Thr Tyr Val Pro Lys Glu Phe Asn Ala Glu Thr Phe Thr Phe His
                565                 570                 575

Ala Asp Ile Cys Thr Leu Ser Glu Lys Glu Arg Gln Ile Lys Lys Gln
            580                 585                 590

Thr Ala Leu Val Glu Leu Val Lys His Lys Pro Lys Ala Thr Lys Glu
            595                 600                 605

Gln Leu Lys Ala Val Met Asp Asp Phe Ala Ala Phe Val Glu Lys Cys
            610                 615                 620

Cys Lys Ala Asp Asp Lys Glu Thr Cys Phe Ala Glu Glu Gly Lys Lys
625                 630                 635                 640

Leu Val Ala Ala Ser Arg Ala Ala Leu Gly Leu
                645                 650

<210> SEQ ID NO 13
<211> LENGTH: 271
<212> TYPE: PRT
<213> ORGANISM: Artificial sequence
<220> FEATURE:
<223> OTHER INFORMATION: Homo sapiens

<400> SEQUENCE: 13

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Gly Ser Ala Gly Ser Ala Ala Gly Ser Gly Glu Phe Asp Lys Thr
        35                  40                  45

His Thr Cys Pro Pro Cys Pro Ala Pro Glu Ala Ala Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Asp Glu Leu Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205
```

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly
            260                 265                 270

<210> SEQ ID NO 14
<211> LENGTH: 279
<212> TYPE: PRT
<213> ORGANISM: Artificial sequence
<220> FEATURE:
<223> OTHER INFORMATION: Homo sapiens

<400> SEQUENCE: 14

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Ala Pro Ala Pro Ala Pro Ala Pro Ala Pro Ala Pro Ala Pro Ala
        35                  40                  45

Pro Ala Pro Ala Pro Asp Lys Thr His Thr Cys Pro Pro Cys Pro Ala
50                  55                  60

Pro Glu Ala Ala Gly Gly Pro Ser Val Phe Leu Phe Pro Pro Lys Pro
65                  70                  75                  80

Lys Asp Thr Leu Met Ile Ser Arg Thr Pro Glu Val Thr Cys Val Val
                85                  90                  95

Val Asp Val Ser His Glu Asp Pro Glu Val Lys Phe Asn Trp Tyr Val
            100                 105                 110

Asp Gly Val Glu Val His Asn Ala Lys Thr Lys Pro Arg Glu Glu Gln
        115                 120                 125

Tyr Asn Ser Thr Tyr Arg Val Val Ser Val Leu Thr Val Leu His Gln
    130                 135                 140

Asp Trp Leu Asn Gly Lys Glu Tyr Lys Cys Lys Val Ser Asn Lys Ala
145                 150                 155                 160

Leu Pro Ala Pro Ile Glu Lys Thr Ile Ser Lys Ala Lys Gly Gln Pro
                165                 170                 175

Arg Glu Pro Gln Val Tyr Thr Leu Pro Pro Ser Arg Asp Glu Leu Thr
            180                 185                 190

Lys Asn Gln Val Ser Leu Thr Cys Leu Val Lys Gly Phe Tyr Pro Ser
        195                 200                 205

Asp Ile Ala Val Glu Trp Glu Ser Asn Gly Gln Pro Glu Asn Asn Tyr
    210                 215                 220

Lys Thr Thr Pro Pro Val Leu Asp Ser Asp Gly Ser Phe Phe Leu Tyr
225                 230                 235                 240

Ser Lys Leu Thr Val Asp Lys Ser Arg Trp Gln Gln Gly Asn Val Phe
                245                 250                 255

Ser Cys Ser Val Met His Glu Ala Leu His Asn His Tyr Thr Gln Lys
            260                 265                 270

Ser Leu Ser Leu Ser Pro Gly
        275

<210> SEQ ID NO 15

<211> LENGTH: 295
<212> TYPE: PRT
<213> ORGANISM: Artificial sequence
<220> FEATURE:
<223> OTHER INFORMATION: Homo sapiens

<400> SEQUENCE: 15

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Ala Glu Ala Ala Ala Lys Glu Ala Ala Lys Glu Ala Ala
        35                  40                  45

Lys Ala Leu Glu Ala Glu Ala Ala Lys Glu Ala Ala Lys Glu
    50                  55                  60

Ala Ala Ala Lys Ala Asp Lys Thr His Thr Cys Pro Pro Cys Pro Ala
65                  70                  75                  80

Pro Glu Ala Ala Gly Gly Pro Ser Val Phe Leu Phe Pro Pro Lys Pro
                85                  90                  95

Lys Asp Thr Leu Met Ile Ser Arg Thr Pro Glu Val Thr Cys Val Val
            100                 105                 110

Val Asp Val Ser His Glu Asp Pro Glu Val Lys Phe Asn Trp Tyr Val
            115                 120                 125

Asp Gly Val Glu Val His Asn Ala Lys Thr Lys Pro Arg Glu Glu Gln
        130                 135                 140

Tyr Asn Ser Thr Tyr Arg Val Val Ser Val Leu Thr Val Leu His Gln
145                 150                 155                 160

Asp Trp Leu Asn Gly Lys Glu Tyr Lys Cys Lys Val Ser Asn Lys Ala
                165                 170                 175

Leu Pro Ala Pro Ile Glu Lys Thr Ile Ser Lys Ala Lys Gly Gln Pro
            180                 185                 190

Arg Glu Pro Gln Val Tyr Thr Leu Pro Pro Ser Arg Asp Glu Leu Thr
        195                 200                 205

Lys Asn Gln Val Ser Leu Thr Cys Leu Val Lys Gly Phe Tyr Pro Ser
210                 215                 220

Asp Ile Ala Val Glu Trp Glu Ser Asn Gly Gln Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Lys Leu Thr Val Asp Lys Ser Arg Trp Gln Gln Gly Asn Val Phe
            260                 265                 270

Ser Cys Ser Val Met His Glu Ala Leu His Asn His Tyr Thr Gln Lys
        275                 280                 285

Ser Leu Ser Leu Ser Pro Gly
    290                 295

<210> SEQ ID NO 16
<211> LENGTH: 275
<212> TYPE: PRT
<213> ORGANISM: Artificial sequence
<220> FEATURE:
<223> OTHER INFORMATION: Homo sapiens

<400> SEQUENCE: 16

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr

```
                      20                  25                  30
Asp Arg Gly Gly Gly Ser Gly Gly Gly Ser Gly Gly Gly
        35                  40                  45

Ser Asp Lys Thr His Thr Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

His Glu Asp Pro Glu Val Lys Phe Asn Trp Tyr Val Asp Gly Val Glu
            100                 105                 110

Val His Asn Ala Lys Thr Lys Pro Arg Glu Glu Gln Tyr Asn Ser Thr
            115                 120                 125

Tyr Arg Val Val Ser Val Leu Thr Val Leu His Gln Asp Trp Leu Asn
        130                 135                 140

Gly Lys Glu Tyr Lys Cys Lys Val Ser Asn Lys Ala Leu Pro Ala Pro
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Arg Asp Glu Leu Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Lys Leu Thr
225                 230                 235                 240

Val Asp Lys Ser Arg Trp Gln Gln Gly Asn Val Phe Ser Cys Ser Val
                245                 250                 255

Met His Glu Ala Leu His Asn His Tyr Thr Gln Lys Ser Leu Ser Leu
            260                 265                 270

Ser Pro Gly
        275

<210> SEQ ID NO 17
<211> LENGTH: 19
<212> TYPE: PRT
<213> ORGANISM: Homo sapiens

<400> SEQUENCE: 17

Met Glu Thr Pro Ala Gln Leu Leu Phe Leu Leu Leu Trp Leu Pro Asp
1               5                   10                  15

Thr Thr Gly
```

GLP-2 ANALOGS AND PEPTIBODIES FOR ADMINISTRATION BEFORE, DURING OR AFTER SURGERY

CROSS-REFERENCE TO RELATED APPLICATIONS

This application is a 371 National Stage of PCT/US18/59175, filed Nov. 5, 2018, which claims priority pursuant to 35 U.S.C. § 119(e) to U.S. Provisional Application No. 62/582,055, filed on Nov. 6, 2017, the disclosure of which are herein incorporated by reference in their entirety.

BACKGROUND

The estimated prevalence of short bowel syndrome (SBS) patients with non-malignant disease requiring home parenteral nutrition (HPN) is at least 40 per million of the U.S. population. SBS usually results from surgical resection of some or most of the small intestine for conditions such as Crohn's disease, mesenteric infarction, volvulus, trauma, congenital anomalies, and multiple strictures due to adhesions or radiation. Surgical resection may also include resection of all or part of the colon. SBS patients suffer from malabsorption that may lead to malnutrition, dehydration and weight loss. Some patients can maintain their protein and energy balance through hyperphagia; more rarely they can sustain fluid and electrolyte requirements to become independent from parenteral fluid.

Post-translational processing of proglucagon generates glucagon-like peptide-2 (GLP-2), a 33 amino acid intestinotrophic peptide hormone. GLP-2 acts to slow gastric emptying, reduce gastric secretions and increase intestinal blood flow. GLP-2 also stimulates growth of the large and small intestine at least by enhancing crypt cell proliferation and villus length so as to increase the surface area of the mucosal epithelium.

These effects suggest that GLP-2 can be used to treat a wide variety of gastrointestinal conditions. Demonstrated specific and beneficial effects of GLP-2 in the small intestine have raised much interest as to the use of GLP-2 in the treatment of intestinal disease or injury (Sinclair and Drucker, Physiology 2005: 357-65). Furthermore GLP-2 has been shown to prevent or reduce mucosal epithelial damage in a wide number of preclinical models of gut injury, including chemotherapy-induced mucositis, ischemia-reperfusion injury, dextran sulfate-induced colitis and genetic models of inflammatory bowel disease (Sinclair and Drucker, Physiology 2005:357-65).

GLP-2 has a short half life that limits its use as a therapeutic because rapid in vivo cleavage of GLP-2 by dipeptidyl peptidase IV (DPP-IV) yields an essentially inactive peptide. Teduglutide, a GLP-2 therapeutic, has a substantially extended half life due to substitution of alanine-2 with glycine. Teduglutide has shown therapeutic promise in treating short bowel syndrome (SBS), which usually results from surgical resection of some or most of the small intestine for conditions such as Crohn's disease, mesenteric infarction, volvulus, trauma, congenital anomalies, and multiple strictures due to adhesions or radiation. Surgical resection may also include resection of all or part of the colon. SBS patients suffer from malabsorption that may lead to malnutrition, dehydration and weight loss. Some patients can maintain their protein and energy balance through hyperphagia, yet it is even rarer that patients can sustain fluid and electrolyte requirements to become independent from parenteral fluid.

SBS patients with end jejunostomy and no colon have low basal GLP-2 levels and limited meal-stimulated GLP-2 secretion due to removal of GLP-2 secreting L-cells, which are located primarily in the terminal ileum and colon. This GLP-2 deficiency results in a minimal adaptive response following resection and could explain the gastric hypersecretion, rapid intestinal transit and lack of intestinal adaptation observed in these SBS patients. Jeppesen et al. (Gastroenterology 2001; 120:806-815) have described positive benefit in an open-label study using pharmacologic doses of native GLP-2 in SBS jejunostomy patients. There was significant improvement in intestinal wet weight absorption and a more modest improvement in energy absorption that led to an increase in body weight, lean body mass and a rise in urinary creatinine excretion. In contrast, SBS patients with colon-in-continuity have elevated basal endogenous GLP-2 levels resulting in an adaptive response to resection characterized by improved wet weight gain and energy absorption. The potential for added benefit of pharmacologic doses of GLP-2 receptor agonists in these patients is not obvious and has not been studied.

There is a need to develop improved ways of administering GLP-2 analogs to treat SBS and other conditions that arise from surgical resection of the small intestine.

BRIEF DESCRIPTION TO THE DRAWINGS

Figure 6:
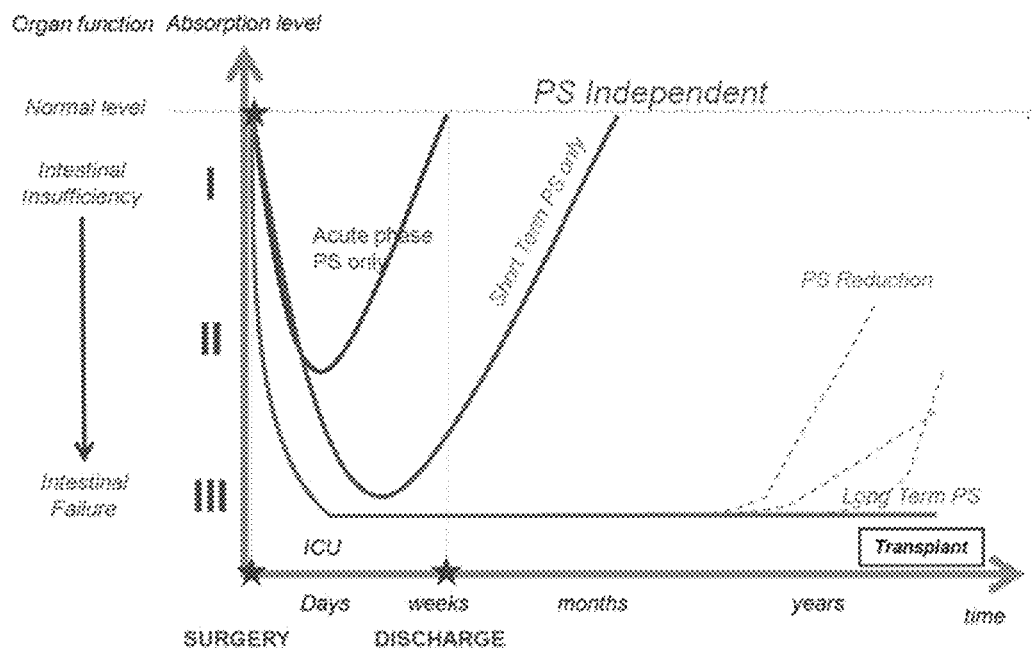

FIG. 6 is a graph showing three different stages of intestinal insufficiency that can develop post-surgery on the Y-axis and time on the X-axis. Administration of h(Gly2)GLP-2 (teduglutide) and/or a GLP-2 peptibody may promote intestinal growth over a period of days or weeks, such as by increasing length of villi and depth of crypts. Such growth may allow for improved intestinal absorption and reduced need for parenteral nutrition (PN) support.

SUMMARY OF THE INVENTION

In one aspect is provided a method of treating a patient who has undergone surgery and has short bowel syndrome. The method comprises administering h(Gly2)GLP-2, a GLP-2 analog, and/or a GLP-2 peptibody to the patient within a period of 48 hours after surgery. In some embodiments, the method comprises administering a GLP-2 peptibody to the patient within a period of 48 hours after surgery. In some embodiments, the GLP-2 peptibody comprises the sequence set forth in SEQ ID NO: 2. In some embodiments, the GLP-2 peptibody comprises the sequence set forth in SEQ ID NO: 4. In some embodiments, the GLP-2 peptibody is administered subcutaneously to the patient at a dose of about 1.4 mg/kg, e.g., 1.4 mg/kg.

In some embodiments, the h(Gly2)GLP-2, a GLP-2 analog, and/or a GLP-2 peptibody is administered to the patient 24 hours after surgery, 18 hours after surgery, 12 hours after surgery, 9 hours after surgery, 6 hours after surgery, three hours after surgery, two hours after surgery, or one hour after surgery. After surgery, h(Gly2)GLP-2 or the GLP-2 analog may be administered about every 6, 7, 8, 9, 10, 11, 12, 13, 14, 15, 16, 17, 18, 19, 20, 21, 22, 23 or 24 hours over a period of one day, two days, three days, four days, five days, six days or seven days. After surgery, the GLP-2 peptibody may be administered once in a subcutaneous or intravenous formulation. The GLP-2 peptibody may again be administered three, four, five, six, seven, or more days after the first dose.

In some embodiments, the patient is receiving parenteral nutrition. The parenteral nutrition support may be short term, medium term, or long term. See, e.g., FIG. 6. In some embodiments, the patient receives an amount of parenteral nutrition each week, with the method effective to reduce the amount of parenteral nutrition received by the patient. In some embodiments, the method is effective to eliminate a need for the patient to receive parenteral nutrition. In some embodiments, the patient has short bowel syndrome secondary to one or more of Crohn's disease, mesenteric infarction, volvulus, multiple strictures due to adhesions or radiation, and vascular ischemia.

In some embodiments, the patient has one or more of a) limited, but some detectable, meal-stimulated GLP-2 secretion (as compared to a normal healthy individual), b) less, but some detectable, GLP-2 producing tissue (as compared to a normal healthy individual), and c) elevated basal levels of endogenous GLP-2 (as compared to a normal healthy individual).

In some embodiments, the method is effective to increase intestinal wet weight absorption, increase intestinal energy absorption, or decrease fecal weight wet.

In another aspect is provided a method of treating a patient who is undergoing surgery and is expected to develop short bowel syndrome after surgery. The method comprises administering h(Gly2)GLP-2, a GLP-2 analog, and/or a GLP-2 peptibody to the patient during a surgery. In some embodiments, h(Gly2)GLP-2 and/or a GLP-2 peptibody is administered to the patient within a period of 48 hours after the surgery. In some embodiments, the method comprises administering a GLP-2 peptibody to the patient within a period of 48 hours after surgery. In some embodiments, the GLP-2 peptibody comprises any of the sequences set forth in SEQ ID NOS: 2-16. In some embodiments, the GLP-2 peptibody comprises the sequence set forth in SEQ ID NO: 2. In some embodiments, the GLP-2 peptibody comprises the sequence set forth in SEQ ID NO: 4. In some embodiments, the GLP-2 peptibody is administered subcutaneously to the patient at a dose of about 1.4 mg/kg, e.g., 1.4 mg/kg.

In some embodiments, the (Gly2)GLP-2, a GLP-2 analog, and/or a GLP-2 peptibody is administered to the patient 24 hours after surgery, 18 hours after surgery, 12 hours after surgery, 9 hours after surgery, 6 hours after surgery, three hours after surgery, two hours after surgery, or one hour after surgery. After surgery, h(Gly2)GLP-2 or the GLP-2 analog may be administered about every 6, 7, 8, 9, 10, 11, 12, 13, 14, 15, 16, 17, 18, 19, 20, 21, 22, 23 or 24 hours over a period of one day, two days, three days, four days, five days, six days or seven days. After surgery, the GLP-2 peptibody may be administered once in a subcutaneous or intravenous formulation. The GLP-2 peptibody may again be administered three, four, five, six, seven, or more days after the first dose.

In some embodiments, the patient is expected to receive parenteral nutrition after the surgery. The parenteral nutrition support may be short term, medium term, or long term. See, e.g., FIG. 6. In some embodiments, the patient is expected to receive an amount of parenteral nutrition each week, with the method effective to reduce the amount of parenteral nutrition received by the patient. In some embodiments, the method is effective to eliminate a need for the patient to receive parenteral nutrition. In some embodiments, the patient has short bowel syndrome secondary to one or more of Crohn's disease, mesenteric infarction, volvulus, multiple strictures due to adhesions or radiation, and vascular ischemia.

In some embodiments, the patient has one or more of a) limited, but some detectable, meal-stimulated GLP-2 secretion (as compared to a normal healthy individual), b) less, but some detectable, GLP-2 producing tissue (as compared to a normal healthy individual), and c) elevated basal levels of endogenous GLP-2 (as compared to a normal healthy individual). In some embodiments, the method is effective to increase intestinal wet weight absorption, increase intestinal energy absorption, or decrease fecal weight wet.

In another aspect is provided a method of treating a patient who is expected to develop short bowel syndrome after a surgery. The method comprises administering h(Gly2)GLP-2, a GLP-2 analog, and/or a GLP-2 peptibody to the patient before the surgery.

In some embodiments, the GLP-2 peptibody is administered to the patient. In some embodiments, the GLP-2 peptibody comprises any of the sequences set forth in SEQ ID NOS: 2-16. In some embodiments, the GLP-2 peptibody comprises the sequence set forth in SEQ ID NO: 2. In some embodiments, the GLP-2 peptibody comprises the sequence set forth in SEQ ID NO: 4. In some embodiments, the GLP-2 peptibody is administered subcutaneously to the patient at a dose of about 1.4 mg/kg, e.g., 1.4 mg/kg.

In some embodiments, the h(Gly2)GLP-2 and/or the GLP-2 peptibody is administered to the patient at least once within one month before the surgery. h(Gly2)GLP-2 or the GLP-2 analogue may be administered once as soon as 24 hours before surgery, 18 hours before surgery, 12 hours before surgery, 9 hours before surgery, 6 hours before surgery, three hours before surgery, two hours before surgery, or one hour before surgery. Multiple administrations of h(Gly2)GLP-2 or the GLP-2 analog can be undertaken every 6, 7, 8, 9, 10, 11, 12, 13, 14, 15, 16, 17, 18, 19, 20, 21, 22, 23 or 24 hours over a period of one day, two days, three days, four days, five days, six days or seven days before surgery. Before surgery, the GLP-2 peptibody may be administered once in a subcutaneous or intravenous formulation. The GLP-2 peptibody may again be administered three, four, five, six, seven, or more days after the first dose.

In some embodiments, the patient is expected to receive parenteral nutrition after the surgery. The parenteral nutrition support may be short term, medium term, or long term. See, e.g., FIG. 6. In some embodiments, the patient is expected to receive an amount of parenteral nutrition each week and the method is effective to reduce the amount of parenteral nutrition received by the patient. In some embodiments, the method is effective to eliminate a need for the patient to receive parenteral nutrition. In some embodiments, after the surgery the patient is expected to develop short bowel syndrome secondary to one or more of Crohn's disease, mesenteric infarction, volvulus, multiple strictures due to adhesions or radiation and vascular ischemia.

In some embodiments, the patient is expected to develop after surgery one or more of a) limited, but some detectable, meal-stimulated GLP-2 secretion (as compared to a normal healthy individual), b) less, but some detectable, GLP-2 producing tissue (as compared to a normal healthy individual), and c) elevated basal levels of endogenous GLP-2 (as compared to a normal healthy individual).

Any of the above methods may be effective to increase intestinal wet weight absorption, increase intestinal energy absorption, or decrease fecal weight wet.

DETAILED DESCRIPTION OF THE INVENTION

Described herein are methods of administering teduglutide, glucagon-like peptide (GLP-2) peptibodies and other GLP-2 analogs, before surgery, during surgery, or within a period of time after surgery. Generally, surgery refers to intestinal resection that would give rise to short bowel syndrome (SBS). Surgery may also include other operations that may exacerbate SBS. A goal of administering teduglutide, GLP-2 peptibodies and GLP-2 analogs before surgery, during surgery, or within a period of time after surgery is to increase intestinal absorption after surgery so as to reduce the degree of parenteral nutrition required. The parenteral nutrition support may be short term, medium term, or long term. See, e.g., FIG. 6. Administration of GLP-2 peptibodies, teduglutide or other GLP-2 analogs before surgery or during surgery may allow for avoidance of short term parenteral nutrition, or at least greatly decrease the time during which short term parenteral nutrition is needed. Also, administration of GLP-2 peptibodies, teduglutide or other GLP-2 analogs after surgery may decrease the time period during which short term and medium term parenteral nutrition is needed. Administration of GLP-2 peptibodies, teduglutide or other GLP-2 analogs may reduce inflammation or enhance the rate of small intestinal wound healing, which may in turn decrease the time period during which short term and medium term parenteral nutrition is needed. The methods herein may avoid or minimize complications of weaning a patient from parenteral nutrition.

Various methods are provided of treating a patient having short bowel syndrome who presents with colon-in-continuity with remnant small intestine by administering h(Gly2) GLP-2, a GLP-2 analog and/or a GLP-2 peptibody to the patient before, during, or after surgery. Any of h(Gly2)GLP-2, a GLP-2 analog and/or a GLP-2 peptibody may be PEGylated, attached to PEG, or otherwise conjugated to PEG at one or more amino acids. The PEG may be of any molecular weight and degree of branching suitable to increase the in vivo half life of the h(Gly2)GLP-2, GLP-2 analog, or even the GLP-2 peptibody.

h(Gly2)GLP-2 comprises the following peptide sequence:

(SEQ ID NO: 1)
HGDGSFSDEMNTILDNLAARDFINWLIQTKITD.

GLP-2 peptibodies may include GLP-2 fused to an Fc sequence or an albumin sequence. Exemplary GLP-2 peptibodies include one or more of the following:

a) a GLP-2 peptibody comprising the amino acid sequence of HGDGSFSDEMNTILDNLAARDFINWLIQT-KITDGGGGGDKTHTCPPCPAPEAAGGPSVFL FPPKPKDTLMISRTPEVTCVVVDVSHEDPE-VKFNWYVDGVEVHNAKTKPREEQYNSTY RVVSVLTVLHQDWLNGKEYKCKVSNKALPA-PIEKTISKAKGQPREPQVYTLPPSRDELT KNQVSLT-CLVKGFYPSDIAVEWESNGQPEN-NYKTTPPVLDSDGSFFLYSKLTVDKSRWQ QGNVFSCSVMHEALHNHYTQKSLSLSPG (SEQ ID NO: 2), or a sequence having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to such amino acid sequence, b) a GLP-2 peptibody comprising the amino acid sequence of HGDGSFSDEMNTILDNLAARDFINWLIQT-KITDGGGGGDKTHTCPPCPAPEAAGGPSVFL FPPKPKDTLMISRTPEVTCVVVDVSHEDPE-VKFNWYVDGVEVHNAKTKPREEQYNSTY RVVSVLTVLHQDWLNGKEYKCKVSNKALPA-PIEKTISKAKGQPREPQVYTLPPSRDELT KNQVSLT-CLVKGFYPSDIAVEWESNGQPEN-NYKTTPPVLDSDGSFFLYSKLTVDKSRWQ QGNVFSCSVMHEALHNHYTQKSLSLSPGK (SEQ ID NO: 3), or a sequence having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to such amino acid sequence, c) a GLP-2 peptibody comprising the amino acid sequence of HGDGSFSDEMNTILDNLAARDFINWLIQT-KITDGGGGSGGGGSGGGGSDKTHTCPPCPA PEAAGGPSVFLFPPKPKDTLMISRTPE-VTCVVVDVSHEDPEVKFNWYVDGVEVHNAKT KPREEQYN-STYRVVSVLTVLHQDWLNGKEYKCKVSNKALPA-PIEKTISKAKGQPREPQ VYTLPPSRDELTKNQVSLT-CLVKGFYPSDIAVEWESNGQPENNYKTTPPVLDSDG-SFFLY SKLTVDKSRWQQGNVFSCSVMHEALHN-HYTQKSLSLSPG (SEQ ID NO: 4), or a sequence having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to such amino acid sequence, d) a GLP-2 peptibody comprising the amino acid sequence of HGDGSFSDEMNTILDNLAARDFINWLIQT-KITDGGGGSGGGGSGGGGSDKTHTCPPCPA PEAAGGPSVFLFPPKPKDTLMISRTPE-VTCVVVDVSHEDPEVKFNWYVDGVEVHNAKT KPREEQYN-STYRVVSVLTVLHQDWLNGKEYKCKVSNKALPA-PIEKTISKAKGQPREPQ VYTLPPSRDELTKNQVSLT-CLVKGFYPSDIAVEWESNGQPENNYKTTPPVLDSDG-SFFLY SKLTVDKSRWQQGNVFSCSVMHEALHN-HYTQKSLSLSPGK (SEQ ID NO: 5), or a sequence having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to such amino acid sequence, e) a GLP-2 peptibody comprising the amino acid sequence of HGDGSFSDEMNTILDNLAARDFINWLIQT-KITDDKTHTCPPCPAPEAAGGPSVFLFPPKP KDTLMISRTPEVTCVVVDVSHEDPE-VKFNWYVDGVEVHNAKTKPREEQYNSTYRVVS VLTVLHQDWLNGKEYKCKVSNKALPA-PIEKTISKAKGQPREPQVYTLPPSRDELTKNQV SLT-CLVKGFYPSDIAVEWESNGQPEN- NYKTTPPVLDSDGSFFLYSKLTVDKSRWQQGNVFSCSVMHEALHNHYTQKSLSLSPG (SEQ ID NO: 6), or a sequence having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to such amino acid sequence, f) a GLP-2 peptibody comprising the amino acid sequence of HGDGSFSDEMNTILDNLAARDFINWLIQTKITDGGGGGGSGGGGSGGGGSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREP QVYTLPPSRDELTKNQVSLTCLVKGFYPSDIAVEWESNGQPENNYKTTPPVLDSDGSFFL YSKLTVDKSRWQQGNVFSCSVMHEALHNHYTQKSLSLSPG (SEQ ID NO: 7), or a sequence having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to such amino acid sequence, g) a GLP-2 peptibody comprising the amino acid sequence of HGDGSFSDEMNTILDNLAARDFINWLIQTKITDGAPGGGGGAAAAAGGGGGGAPGGGGGAAAAAGGGGGGAPGGGGGAAAAAGGGGGGAPDKTHTCPPCPAPEAAGGPSVFLFPP KPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO: 8), or a sequence having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to such amino acid sequence, h) a GLP-2 peptibody comprising the amino acid sequence of HGDGSFSDEMNTILDNLAARDFINWLIQTKITDGGGGGGGDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLYSKLTVDKS RWQQGNVFSCSVMHEALHNHYTQKSLSLSPG (SEQ ID NO: 9), or a sequence having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to such amino acid sequence, i) a GLP-2 peptibody comprising the amino acid sequence of HGDGSFSDEMNTILDNLAARDFINWLIQTKITDGGGGSGGGGSDKTHTCPPCPAPEAAG GPSVFLEPPKPKDTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQPREPQVYTLPPS RDELTKNQVSLTCLVKGFYPSDIAVEWESNGQPENNYKTTPPVLDSDGSFFLYSKLTVD KSRWQQGNVFSCSVMHEALHNHYTQKSLSLSPG (SEQ ID NO: 10), or a sequence having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to such amino acid sequence, j) a GLP-2 peptibody comprising the amino acid sequence of HGDGSFSDEMNTILDNLAARDFINWLIQTKITDGGGGGGSGGGGSGGGGSDAHKSEVA HRFKDLGEENFKALVLIAFAQYLQQCPFEDHVKLVNEVTEFAKTCVADESAENCDKSLH TLFGDKLCTVATLRETYGEMADCCAKQEPERNECFLQHKDDNPNLPRLVRPEVDVMCT AFHDNEETFLKKYLYEIARRHPYFYAPELLFFAKRYKAAFTECCQAADKAACLLPKLDE LRDEGKASSAKQRLKCASLQKFGERAFKAWAVARLSQRFPKAEFAEVSKLVTDLTKVH TECCHGDLLECADDRADLAKYICENQDSISSKLKECCEKPLLEKSHCIAEVENDEMPADL PSLAADFVESKDVCKNYAEAKDVFLGMFLYEYARRHPDYSVVLLLRLAKTYKTTLEKC CAAADPHECYAKVEDEFKPLVEEPQNLIKQNCELFEQLGEYKEQNALLVRYTKKVPQVS TPTLVEVSRNLGKVGSKCCKHPEAKRMPCAEDYLSVVLNQLCVLHEKTPVSDRVTKCC TESLVNRRPCFSALEVDETYVPKEFNAETFTFHADICTLSEKERQIKKQTALVELVKHKP KATKEQLKAVMDDFAAFVEKCCKADDKETCFAEEGKKLVAASRAALGL (SEQ ID NO: 11), or a sequence having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to such amino acid sequence, k) a GLP-2 peptibody comprising the amino acid sequence of HGDGSFSDEMNTILDNLAARDFINWLIQTKITDHGDGSFSDEMNTILDNLAARDFINWLI QTKITDDAHKSEVAHRFKDLGEENFKALVLIAFAQYLQQCPFEDHVKLVNEVTEFAKTC VADESAENCDKSLHTLFGDKLCTVATLRETYGEMADCCAKQEPERNECFLQHKDDNPN LPRLVRPEVDVMCTAFHDNEETFLKKYLYEIARRHPYFYAPELLFFAKRYKAAFTECCQ AADKAACLLPKLDELRDEGKASSAKQRLKCASLQKFGERAFKAWAVARLSQRFPKAEF AEVSKLVTDLTKVHTECCHGDLLECADDRADLAKYICENQDSISSKLKECCEKPLLEKS HCIAEVENDEMPADLPSLAADFVESKDVCKNYAEAKDVFLGMFLYEYARRHPDYSVVL LLRLAKTYKTTLEKCCAAADPHECYAKVEDEFKPLVEEPQNLIKQNCELFEQLGEYKEQ NALLVRYTKKVPQVSTPTLVEVSRNLGKVGSKCCKHPEAKRMPCAEDYLSVVLNQLCV LHEKTPVSDRVTKCCTESLVNRRPCFSALEVDETYVPKEFNAETFTFHADICTLSEKERQI KKQTALVELVKHKPKATKEQLKAVMDDFAAFVEKCCKADDKETCFAEEGKKLVAASR AALGL (SEQ ID NO: 12), or a sequence having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to such amino acid sequence;

l) a GLP-2 peptibody comprising the amino acid sequence of HGDGSFSDEMNTILDNLAARDFINWLIQTKITDGSAGSAAGSGEFDKTHTCPPCPAPEAA GGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGSFFLYSKLTV DKSRWQQGNVFSCSVMHEALHNHYTQKSLSLSPG (SEQ ID NO: 13), or a sequence having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to such amino acid sequence;

m) a GLP-2 peptibody comprising the amino acid sequence of HGDGSFSDEMNTILDNLAARDFINWLIQT-KITDAPAPAPAPAPAPAPAPAPAPDKTHTCP PCPA-PEAAGGPSVFLFPPKPKDTLMISRTPE-VTCVVVDVSHEDPEVKFNWYVDGVEVHN AKTKPREEQYN-STYRVVSVLTVLHQDWLNGKEYKCKVSNKALPA-PIEKTISKAKGQPR EPQVYTLPPSRDELTKNQVSLT-CLVKGFYPSDIAVEWESNGQPENNYKTTPPVLDSDG-SF FLYSKLTVDKSRWQQGNVFSCSVMHEALHN-HYTQKSLSLSPG (SEQ ID NO: 14), or a sequence having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to such amino acid sequence;

n) a GLP-2 peptibody comprising the amino acid sequence of HGDGSFSDEMNTILDNLAARDFINWLIQT-KITDAEAAAKEAAAKEAAAKALEAEAAAK EAAAKEAAAKADKTHTCPPCPA-PEAAGGPSVFLFPPKPKDTLMISRTPEVTCVVVDVSH EDPEVKFNWYVDGVEVHNAKTKPREEQYN-STYRVVSVLTVLHQDWLNGKEYKCKVS NKALPA-PIEKTISKAKGQPREPQVYTLPPSRDELTKNQVSLT-CLVKGFYPSDIAVEWESN GQPENNYKTTPPVLDSDGSFFLYSK-LTVDKSRWQQGNVFSCSVMHEALHNHYTQKSLS LSPG (SEQ ID NO: 15), or a sequence having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to such amino acid sequence;

o) a GLP-2 peptibody comprising the amino acid sequence of HGDGSFSDEMNTILDNLAARDFINWLIQT-KITDRGGGGSGGGGSGGGGSDKTHTCPPCP APEAAGGPSVFLFPPKPKDTLMISRTPE-VTCVVVDVSHEDPEVKFNWYVDGVEVHNAK TKPREEQYN-STYRVVSVLTVLHQDWLNGKEYKCKVSNKALPA-PIEKTISKAKGQPREPQ VYTLPPSRDELTKNQVSLT-CLVKGFYPSDIAVEWESNGQPENNYKTTPPVLDSDG-SFFLY SKLTVDKSRWQQGNVFSCSVMHEALHN-HYTQKSLSLSPG (SEQ ID NO: 16), or a sequence having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to such amino acid sequence;

or any of the GLP-2 peptibody sequences described in U.S. Provisional Application No. 62/548,601, filed Aug. 22, 2017.

In GLP-2 peptibodies, a linker sequence may be present between the GLP-2 sequence and another sequence, such as IgG1 Fc or human serum albumin. The GLP-2 peptibody K274 has the amino acid sequence set forth in SEQ ID NO: 4. The GLP-2 peptibody B264 has the amino acid sequence set forth in SEQ ID NO: 2.

The GLP-2 peptibody may be processed a GLP-2 precursor polypeptide that comprises a signal peptide directly linked with GLP-2. Any number of signal peptides may be used, with an exemplary signal peptide having the following sequence: METPAQLLFLLLWLPDTTG (SEQ ID NO: 17).

h(Gly2)GLP-2 is described in U.S. Pat. No. 7,847,061, issued Dec. 7, 2010. GLP-2 peptibodies are described in U.S. Provisional Application No. 62/548,601, filed Aug. 22, 2017.

As used herein, the term "subcutaneous tissue", is defined as a layer of loose, irregular connective tissue immediately beneath the skin. For example, the subcutaneous administration may be performed by injecting a composition into areas including, but not limited to, the thigh region, abdominal region, gluteal region, or scapular region. Subcutaneous administration may be accomplished by injecting the composition with a syringe. However, other devices for administration of the formulation are available such as injection devices (e.g., the Inject-ease™ and Genject™ devices); injector pens (such as the GenPen™); needleless devices (e.g., MediJector™ and BioJector™); and subcutaneous patch delivery systems.

As used in this application, the terms "about" and "approximately" are used as equivalents. Any numerals used in this application with or without "about" or "approximately" are meant to cover any normal fluctuations appreciated by one of ordinary skill in the relevant art. As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, the terms "carrier" and "diluent" refer to a pharmaceutically acceptable (e.g., safe and non-toxic for administration to a human) carrier or diluting substance useful for the preparation of a pharmaceutical formulation. Exemplary diluents include sterile water, bacteriostatic water for injection (BWFI), a pH buffered solution (e.g. phosphate-buffered saline), sterile saline solution, Ringer's solution or dextrose solution.

As used herein, the term "fusion protein" or "chimeric protein" refers to a protein created through the joining of two or more originally separate proteins, or portions thereof. In some embodiments, a linker or spacer will be present between each protein.

As used herein, the term "half-life" is the time required for a quantity such as protein concentration or activity to fall to half of its value as measured at the beginning of a time period.

A "GLP-2 peptibody," "GLP-2 peptibody portion," or "GLP-2 peptibody fragment" and/or "GLP-2 peptibody variant" and the like can have, mimic or simulate at least one biological activity, such as but not limited to ligand binding, in vitro, in situ and/or preferably in vivo, of at least one GLP-2 peptide. For example, a suitable GLP-2 peptibody, specified portion, or variant can also modulate, increase, modify, activate, at least one GLP-2 receptor signaling or other measurable or detectable activity. GLP-2 peptibodies may have suitable affinity-binding to protein ligands, for example, GLP-2 receptors, and optionally have low toxicity. The GLP-2 peptibodies can be used to treat patients for extended periods with good to excellent alleviation of symptoms and low toxicity.

As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

As used herein, the term "in vitro" refers to events that occur in an artificial environment, e.g., in a test tube or reaction vessel, in cell culture, etc., rather than within a multi-cellular organism.

As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

As used herein, the term "linker" refers to, in a fusion protein, an amino acid sequence other than that appearing at a particular position in the natural protein and is generally designed to be flexible or to interpose a structure, such as an α-helix, between two protein moieties. A linker is also referred to as a spacer. A linker or a spacer typically does not have biological function on its own.

As used herein, the term "PEG" includes poly(ethylene glycol) in any of its forms, including alkoxy PEG, difunctional PEG, multi-arm PEG, forked PEG, branched PEG, pendent PEG (i.e. PEG or related polymers having one or more functional groups pendent to the polymer backbone), or PEG with degradable linkages therein.

As used herein, the phrase "pharmaceutically acceptable" refers to molecular entities and compositions that are generally regarded as physiologically tolerable.

The term "polypeptide" as used herein refers to a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified. As used herein, the terms "polypeptide" and "peptide" are used inter-changeably. The term "polypeptide" can also refer to proteins.

As used herein, the term "prevent" or "prevention", when used in connection with the occurrence of a disease, disorder, and/or condition, refers to reducing the risk of developing the disease, disorder and/or condition. See the definition of "risk."

As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

PEGylated GLP-2

A wide variety of useful active GLP-2 analogs and derivatives have been described in the literature. See U.S. Pat. No. 5,789,379 issued Jun. 20, 2000; WO02/066511 published Aug. 27, 2003; WO99/43361 published Oct. 14, 1999; WO04/035624 published Apr. 29, 2004 and WO04/085471 published Oct. 7, 2004. Any of these GLP-2 analogs and derivatives may be conjugated to PEG.

Serum half-life may also be prolonged by coupling h(Gly2)GLP-2, GLP-2 analogs, or even GLP-2 peptibodies to polyethylene glycol (PEG) or other related polymers known in the art. Such PEGylation can provide for increased molecular size and decrease surface- and functional group-accessibility. These effects may increase the half life in the plasma, prevent degradation by proteases, decrease immunogenicity and decrease uptake by the liver.

GLP-2 Peptibody

Exemplary GLP-2 peptibodies include, but are not limited to, those comprising a sequence of SEQ ID NOS: 2-16. Any of the GLP-2 peptibody sequences above may further comprise a lysine (K) at the C-terminus. Also, the GLP-2 sequence in the GLP-2 peptibody may incorporate an amino acid substitution that renders the peptide resistant to the endogenous enzyme dipeptidyl peptidase IV (DPP-IV). Such analogs incorporate an appropriate substitution of the Ala2 residue desirably, but not essentially, by a genetically encoded amino acid, to permit recombinant production of the desired protein. Amino acids that can usefully substitute at Alanine-2 to provide GLP-2 analogs that retain GLP-2 receptor agonist activity and are less susceptible to DPP-IV include Gly, D-Ala, Val, Glu, Lys, Arg, Leu and Ile. Still other GLP-2 analogs include those substituted at Met-10 by an amino acid that is less sensitive to oxidation.

The GLP-2 peptibody, GLP-2 analogs or even h(Gly2) GLP-2 can be derivatized, for instance at an internal or substituted lysine, to prolong serum half-life by conjugation with lipophilic groups, with polyethylene glycol groups, the Fc domain of immunoglobulins, with albumin or with any other functional group having the desired effect of reducing the rate at which the peptide is degraded endogenously following its administration. Such derivatized forms may be derivatized analogs of GLP-2, which carry substitutions, such as conserved or non-conserved lysine substitutions, having no appreciable negative effect on GLP-2 receptor activation but allowing for conjugation of the desired functional group. It will be appreciated that these derivatized forms of GLP-2 or of GLP-2 analogs are considered to be GLP-2 receptor agonists if they exert their endogenous effect through the GLP-2 receptor after administration, even if this GLP-2 receptor agonist property is not displayed while in the pro-drug, pre-administration form.

In one aspect is provided a method of treating a patient having short bowel syndrome with non-malignant disease. The patient receives an amount of parenteral nutrition each week, and who presents with colon-in-continuity with remnant small intestine. The method comprises administering h(Gly2)GLP-2, GLP-2 analogs and/or a GLP-2 peptibody to the patient just before surgery, during surgery, or within a period of time after surgery, using a dosing regimen effective to reduce or eliminate the weekly amount of parenteral nutrition received by the patient. In some embodiments, the GLP-2 peptibody comprises the sequence of any of SEQ ID NOS: 2-16. In some embodiments, the GLP-2 peptibody comprises the sequence of SEQ ID NO: 4. In another embodiment, the GLP-2 peptibody is for use in the manufacture of a medicament for treating short bowel syndrome with non-malignant disease just before surgery, during surgery, or within a period of time after surgery.

Some patients can maintain their protein and energy balance through hyperphagia; more rarely they can sustain fluid and electrolyte requirements to become independent from parenteral fluid. Although long-term parenteral nutrition (PN) is lifesaving in patients with intestinal failure, it is expensive, impairs quality of life and is associated with serious complications such as catheter sepsis, venous occlusions and liver failure. Total parenteral nutrition often leads to atrophy of the small intestine, which could lead to increased dependency on PN as the small intestine becomes less able to absorb energy, water and other nutrients due to decreased size. Treatments that amplify absolute intestinal absorption, and eliminate or minimize the need for PN have great potential significance to SBS patients. Administration of one or more of the h(Gly2)GLP-2, GLP-2 analogs and GLP-2 peptibodies before, during, or shortly after surgery can reduce the need for PN, allow for reduced amount and/or time of PN administration, or even allow for avoidance of PN.

Without wishing to be bound by theory, h(Gly2)GLP-2, GLP-2 analogs and GLP-2 peptibodies have numerous activities that include slowing gastric emptying, reducing gastric secretions, increasing intestinal blood-flow and stimulating growth of the small and large intestine. Growth of the small and large intestine can occur by stimulation of crypt cell proliferation and inhibition of enterocyte apoptosis. The surface area of the intestine increases and thus improved absorption of water, nutrients and energy may occur. Such improved absorption can reduce or even eliminate the need for parenteral nutrition.

A dosing regimen effective to treat the SBS patients with colon-in-continuity can comprise delivering the selected GLP-2 receptor agonist to the patient for a time and at a dose sufficient to enhance intestinal absorption. One suitable treatment regimen entails once daily administration of h(Gly2)GLP-2, by subcutaneous injection in the abdomen, thigh or arm, at a dose in the range from 30 to 150 ug/kg/day for a period of about 21 days. h(Gly2)GLP-2 may be administered subcutaneously or intravenously.

The GLP-2 peptibody may also be administered subcutaneously or intravenously. The GLP-2 peptibody can be administered subcutaneously according to a dosage regimen of between 0.02 to 3.0 mg/kg once every 2-14 days. A GLP-2 peptibody may be administered subcutaneously according to a dosage regimen of between 0.02 to 3.0 mg/kg, 0.02 to 0.5 mg/kg, 0.04 to 0.45 mg/kg, 0.08 to 0.4 mg/kg, 0.10 to 0.35 mg/kg, 0.20 to 0.30 mg/kg, 0.02 to 0.05 mg/kg, 0.03 to 0.04 mg/kg, 0.05 to 0.10 mg/kg, 0.10 to 0.15 mg/kg, 0.2 to 0.3 mg/kg, 0.3 to 0.4 mg/kg, 0.4 to 0.5 mg/kg, 0.5 to 0.8 mg/kg, 0.7 to 1.0 mg/kg, 0.9 to 1.2 mg/kg, 1.0 to 1.5 mg/kg, 1.2 to 1.8 mg/kg, 1.5 to 2.0 mg/kg, 1.7 to 2.5 mg/kg, or 2.0 to 3.0 mg/kg.

The administered GLP-2 peptibody may be in a concentration of 10 to 100 mg/mL, 10 to 90 mg/mL, 20 to 80 mg/mL, 25 to 75 mg/mL, 30 to 70 mg/mL, 50 to 100 mg/mL, 60 to 90 mg/mL, about 75 mg/mL, 75 mg/mL, 10 to 20 mg/mL, 15 to 25 mg/mL, 12 to 18 mg/mL, 13-17 mg/mL, 14-16 mg/mL, about 15 mg/mL or 15 mg/mL.

The effects of administration of h(Gly2)GLP-2, a GLP-2 analog or GLP-2 peptibodies pre-surgery, during surgery, or even post-surgery can be rapid, e.g., within 60 hours of administration, within 48 hours of administration, within 36 hours of administration, or within 24 hours of administration. Such administration can rapidly improve GI transit within 48 hours after surgery. Such administration can also enhance stem cell activity and even provide a long-term improvement in wound healing in the small intestine after the surgery.

In some embodiments, administration of h(Gly2)GLP-2, GLP-2 analogs or GLP-2 peptibodies can reduce inflammation from surgery. For example, administration of such 2, 3, 4, 5, or 6 hours before surgery can reduce the inflammatory response from resection of the small intestine. Reduction of the inflammatory response can expedite recovery from surgery and allow for other administrations of h(Gly2)GLP-2, GLP-2 analogs or GLP-2 peptibodies to act more quickly to increase growth of the small and large intestine, e.g. by increasing crypt depth or by increasing villus height.

In some embodiments of pre-surgical and post-surgical administration, the GLP-2 peptibody is administered subcutaneously according to a dosage regimen of between 0.02 to 0.5 mg/kg once every 2-14 days. In some embodiments, the GLP-2 peptibody is administered intravenously according to a dosage regimen of between 0.02 to 3.0 mg/kg once every 2-14 days. In some embodiments, the administered GLP-2 peptibody is in a concentration of 10 to 200 mg/mL.

Treatment candidates include those short bowel syndrome patients who retain at least 50% or more of colon length in continuity with remnant small intestine after the surgery. Such a treatment candidate is identified herein as a patient with >50% colon-in-continuity after the surgery. In other preferred embodiments, the SBS patient with colon-in-continuity has or is expected to have a remnant small intestine at least about 50 cm in length after the surgery which, desirably but not essentially, incorporates at least a portion of the ileum.

In one aspect is provided a method of treating a patient having short bowel syndrome with Crohn's disease or secondary to Crohn's disease. The patient receives an amount of parenteral nutrition each week or is expected to receive an amount of parenteral nutrition each week after surgery, e.g., resection of the small intestine. The patient also presents (or will present after surgery) with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to reduce or eliminate the weekly amount of parenteral nutrition received by the patient. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the compositions described herein are for use in a method of treating short bowel syndrome with Crohn's disease, or secondary to Crohn's disease, the method comprising administering the GLP-2 peptibody just before surgery, during surgery, or within a period of time after surgery. In another embodiment, the GLP-2 peptibody is for use in the manufacture of a medicament for treating short bowel syndrome with Crohn's disease, or secondary to Crohn's disease. The medicament may be administered just before surgery, during surgery, or within a period of time after surgery.

In one aspect is provided a method of treating a patient having short bowel syndrome with mesenteric infarction. The patient receives an amount of parenteral nutrition each week or is expected to receive an amount of parenteral nutrition each week after surgery, e.g., resection of the small intestine. The patient also presents with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to reduce or eliminate the weekly amount of parenteral nutrition received by the patient. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the compositions described herein are for use in a method of treating short bowel syndrome with mesenteric infarction, the method comprising administering the GLP-2 peptibody just before surgery, during surgery, or within a period of time after surgery. In another embodiment, the GLP-2 peptibody is for use in the manufacture of a medicament for treating short bowel syndrome with mesenteric infarction. The medicament may be administered just before surgery, during surgery, or within a period of time after surgery.

In one aspect is provided a method of treating a patient having short bowel syndrome with volvulus or secondary to volvulus. The patient receives an amount of parenteral nutrition each week or is expected to receive an amount of parenteral nutrition each week after surgery, e.g., resection of the small intestine. The patient also presents with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to reduce or eliminate the weekly amount of parenteral nutrition received by the patient. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the compositions described herein are for use in a method of treating short bowel syndrome with volvulus, or secondary to volvulus, the method comprising administering the GLP-2 peptibody just before surgery, during surgery, or within a period of time after surgery. In another embodiment, the GLP-2 peptibody is for use in the manufacture of a medicament for treating short bowel syndrome with volvulus, or secondary to volvulus. The medicament may be administered just before surgery, during surgery, or within a period of time after surgery.

In one aspect is provided a method of treating a patient having short bowel syndrome with congenital intestinal abnormalities. The patient receives an amount of parenteral nutrition each week or is expected to receive an amount of parenteral nutrition each week after surgery, e.g., resection of the small intestine. The patient also presents with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to reduce or eliminate the weekly amount of parenteral nutrition received by the patient. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the compositions described herein are for use in a method of treating short bowel syndrome with congenital intestinal abnormalities, the method comprising administering the GLP-2 peptibody just before surgery, during surgery, or within a period of time after surgery. In another embodiment, the GLP-2 peptibody is for use in the manufacture of a medicament for treating short bowel syndrome with congenital intestinal abnormalities. The medicament may be administered just before surgery, during surgery, or within a period of time after surgery.

In one aspect is provided a method of treating a patient having short bowel syndrome with multiple strictures due to adhesions or radiation. The patient receives an amount of parenteral nutrition each week or is expected to receive an amount of parenteral nutrition each week after surgery, e.g., resection of the small intestine. The patient also presents with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to reduce or eliminate the weekly amount of parenteral nutrition received by the patient. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of treating short bowel syndrome with multiple strictures due to adhesions or radiation, the method comprising administering the GLP-2 peptibody just before surgery, during surgery, or within a period of time after surgery. In another embodiment, the GLP-2 peptibody is for use in the manufacture of a medicament for treating short bowel syndrome with multiple strictures due to adhesions or radiation. The medicament may be administered just before surgery, during surgery, or within a period of time after surgery.

In one aspect is provided a method of treating a patient having short bowel syndrome with vascular ischemia or secondary to vascular ischemia. The patient receives an amount of parenteral nutrition each week or is expected to receive an amount of parenteral nutrition each week after surgery, e.g., resection of the small intestine. The patient also presents with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to reduce or eliminate the weekly amount of parenteral nutrition received by the patient. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of treating short bowel syndrome with vascular ischemia, or secondary to vascular ischemia, the method comprising administering the GLP-2 peptibody just before surgery, during surgery, or within a period of time after surgery. In another embodiment, the GLP-2 peptibody is for use in the manufacture of a medicament for treating short bowel syndrome with vascular ischemia, or secondary to vascular ischemia. The medicament may be administered just before surgery, during surgery, or within a period of time after surgery.

In one aspect is provided a method of treating a patient having short bowel syndrome with limited (as compared to a normal healthy individual), but some detectable, meal-stimulated GLP-2 secretion. The patient receives an amount of parenteral nutrition each week or is expected to receive an amount of parenteral nutrition each week after surgery, e.g., resection of the small intestine. The patient also presents with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to increase meal-stimulated GLP-2 secretion. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method for treating short bowel syndrome in a patient with limited (as compared to a normal healthy individual), but some detectable, meal-stimulated GLP-2 secretion, the method comprising administering the GLP-2 peptibody just before surgery, during surgery, or within a period of time after surgery. In another embodiment, the GLP-2 peptibody is for use in the manufacture of a medicament for treating short bowel syndrome in a patient with limited (as compared to a normal healthy individual), but some detectable, meal-stimulated GLP-2 secretion. The medicament may be administered just before surgery, during surgery, or within a period of time after surgery.

In one aspect is provided a method of treating a patient having short bowel syndrome with at least 25% colon-in-continuity with remnant small intestine. The patient receives an amount of parenteral nutrition each week or is expected to receive an amount of parenteral nutrition each week after surgery, e.g., resection of the small intestine. The method comprises administering h(Gly2)GLP-2, a GLP-2 analog and/or a GLP-2 peptibody to the patient just before surgery, during surgery, or within a period of time after surgery. A dosing regimen is used that is effective to reduce or eliminate the weekly amount of parenteral nutrition received by the patient. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of treating short bowel syndrome with at least 25% colon-in-continuity with remnant small intestine, the method comprising administering the GLP-2 peptibody just before surgery, during surgery, or within a period of time after surgery. In another embodiment, the GLP-2 peptibody is for use in the manufacture of a medicament for treating short bowel syndrome with at least 25% colon-in-continuity with remnant small intestine. The medicament may be administered just before surgery, during surgery, or within a period of time after surgery.

In one aspect is provided a method of treating a patient having short bowel syndrome with less (as compared to a normal healthy individual), but some detectable, GLP-2 producing tissue. The patient receives an amount of parenteral nutrition each week or is expected to receive an amount of parenteral nutrition each week after surgery, e.g., resection of the small intestine. The patient also presents with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to increase the amount of GLP-2 producing tissue of the patient. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of treating short bowel syndrome in a patient having short bowel syndrome with less (as compared to a normal healthy individual), but some detectable, GLP-2 producing tissue, the method comprising administering the GLP-2 peptibody just before surgery, during surgery, or within a period of time after surgery. In another embodiment, the GLP-2 peptibody is for use in the manufacture of a medicament for treating short bowel syndrome in a patient having short bowel syndrome with less (as compared to a normal healthy individual), but some detectable, GLP-2 producing tissue. The medicament may be administered just before surgery, during surgery, or within a period of time after surgery.

In one aspect is provided a method of treating a patient having short bowel syndrome with elevated (as compared to a normal healthy individual) basal levels of endogenous GLP-2. The patient receives an amount of parenteral nutrition each week or is expected to receive an amount of parenteral nutrition each week after surgery, e.g., resection of the small intestine. The patient also presents with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to reduce or eliminate the weekly amount of parenteral nutrition received by the patient. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of treating short bowel syndrome in a patient with elevated (as compared to a normal healthy individual) basal levels of endogenous GLP-2, the method comprising administering the GLP-2 peptibody just before surgery, during surgery, or within a period of time after surgery. In another embodiment, the GLP-2 peptibody is for use in the manufacture of a medicament for treating short bowel syndrome in a patient with elevated (as compared to a normal healthy individual) basal levels of endogenous GLP-2. The medicament may be administered just before surgery, during surgery, or within a period of time after surgery.

In one aspect is provided a method of treating a patient having short bowel syndrome with equal or elevated (as compared to a normal healthy individual) meal stimulated levels of endogenous GLP-2. The patient receives an amount of parenteral nutrition each week or is expected to receive an amount of parenteral nutrition each week after surgery, e.g., resection of the small intestine. The patient also presents with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to reduce or eliminate the weekly amount of parenteral nutrition received by the patient. In some embodiments, the GLP-2 peptibody comprises the sequence of any of SEQ ID NOS: 2-16. In some embodiments, the GLP-2 peptibody comprises the sequence of SEQ ID NO: 4. In another embodiment, the GLP-2 peptibody is for use in a method of treating short bowel syndrome in a patient with elevated (as compared to a normal healthy individual) meal stimulated levels of endogenous GLP-2, the method comprising administering the GLP-2 peptibody just before surgery, during surgery, or within a period of time after surgery. In another embodiment, the GLP-2 peptibody is for use in the manufacture of a medicament for treating short bowel syndrome in a patient with elevated (as compared to a normal healthy individual) meal stimulated levels of endogenous GLP-2. The medicament may be administered just before surgery, during surgery, or within a period of time after surgery.

In one aspect is provided a method of treating a patient having short bowel syndrome with colon-in-continuity and remnant small intestine ranging from about 25 cm to about 200 cm. The patient receives an amount of parenteral nutrition each week or is expected to receive an amount of parenteral nutrition each week after surgery, e.g., resection of the small intestine. The method comprises administering h(Gly2)GLP-2, a GLP-2 analog and/or a GLP-2 peptibody to the patient just before surgery, during surgery, or within a period of time after surgery. A dosing regimen is used that is effective to reduce or eliminate the weekly amount of parenteral nutrition received by the patient. In some embodiments, the GLP-2 peptibody comprises the sequence of any of SEQ ID NOS: 2-16. In some embodiments, the GLP-2 peptibody comprises the sequence of SEQ ID NO: 4. In another embodiment, the GLP-2 peptibody is for use in a method of treating short bowel syndrome in a patient with colon-in-continuity and remnant small intestine ranging from about 25 cm to about 200 cm, just before surgery, during surgery, or within a period of time after surgery. In another embodiment, the GLP-2 peptibody is for use in the manufacture of a medicament for treating short bowel syndrome in a patient with colon-in-continuity and remnant small intestine ranging from about 25 cm to about 200 cm, the method comprising administering the GLP-2 peptibody just before surgery, during surgery, or within a period of time after surgery. In another embodiment, the GLP-2 peptibody is for use in the manufacture of a medicament for treating short bowel syndrome in a patient with colon-in-continuity and remnant small intestine ranging from about 25 cm to about 200 cm. The medicament may be administered just before surgery, during surgery, or within a period of time after surgery.

In one aspect is provided a method of treating a patient having short bowel syndrome with at least about 10% (as compared to a normal healthy individual) endogenous GLP-2 levels in the fed state. The patient receives an amount of parenteral nutrition each week, and who presents with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to increase the endogenous GLP-2 in the fed state of the patient. In some embodiments, the GLP-2 peptibody comprises the sequence of any of SEQ ID NOS: 2-16. In some embodiments, the GLP-2 peptibody comprises the sequence of SEQ ID NO: 4. In another embodiment, the GLP-2 peptibody is for use in a method of treating short bowel syndrome in a patient with at least about 10% (as compared to a normal healthy individual) endogenous GLP-2 levels in the fed state, just before surgery, during surgery, or within a period of time after surgery. In another embodiment, the GLP-2 peptibody is for use in the manufacture of a medicament for treating short bowel syndrome in a patient with at least about 10% (as compared to a normal healthy individual) endogenous GLP-2 levels in the fed state, just before surgery, during surgery, or within a period of time after surgery. The medicament may be administered just before surgery, during surgery, or within a period of time after surgery.

In one aspect is provided a method of treating a patient having short bowel syndrome with colon-in-continuity and at least about 50 cm of remnant small intestine. The patient receives an amount of parenteral nutrition each week or is expected to receive an amount of parenteral nutrition each week after surgery, e.g., resection of the small intestine. The method comprises administering h(Gly2)GLP-2, a GLP-2 analog and/or a GLP-2 peptibody to the patient just before surgery, during surgery, or within a period of time after surgery. A dosing regimen is used that is effective to reduce or eliminate the weekly amount of parenteral nutrition received by the patient. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of treating short bowel syndrome in a patient with colon-in-continuity and at least about 50 cm of remnant small intestine, just before surgery, during surgery, or within a period of time after surgery. In another embodiment, the GLP-2 peptibody is for use in the manufacture of a medicament for treating short bowel syndrome in a patient with colon-in-continuity and at least about 50 cm of remnant small intestine, just before surgery, during surgery, or within a period of time after surgery. The medicament may be administered just before surgery, during surgery, or within a period of time after surgery.

In one aspect is provided a method of decreasing fecal wet weight of a patient having short bowel syndrome. The patient receives an amount of parenteral nutrition each week or is expected to receive an amount of parenteral nutrition each week after surgery, e.g., resection of the small intestine. The patient also presents with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to decrease the fecal wet weight of the patient. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of decreasing fecal wet weight of a patient having short bowel syndrome, the method comprising administering the GLP-2 peptibody just before surgery, during surgery, or within a period of time after surgery. In another embodiment, the GLP-2 peptibody is for use in the manufacture of a medicament for decreasing fecal wet weight of a patient having short bowel syndrome. The medicament may be administered just before surgery, during surgery, or within a period of time after surgery.

Absolute wet weight absorption may be obtained by subtracting fecal wet weight from diet wet weight.

In one aspect is provided a method of increasing urine weight of a patient having short bowel syndrome. The patient receives an amount of parenteral nutrition each week or is expected to receive an amount of parenteral nutrition each week after surgery, e.g., resection of the small intestine. The patient also presents with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to increase the urine weight of the patient. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of increasing urine weight of a patient expected to have short bowel syndrome after surgery, the method comprising administering the GLP-2 peptibody just before surgery, during surgery, or within a period of time after surgery. In another embodiment, the GLP-2 peptibody is for use in the manufacture of a medicament for increasing urine weight of a patient having short bowel syndrome. The medicament may be administered just before surgery, during surgery, or within a period of time after surgery.

In one aspect is provided a method of treating a patient having short bowel syndrome without inflammatory bowel disease. The patient receives an amount of parenteral nutrition each week or is expected to receive an amount of parenteral nutrition each week after surgery, e.g., resection of the small intestine. The patient also presents with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to reduce or eliminate the weekly amount of parenteral nutrition received by the patient. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of treating short bowel syndrome in a patient without inflammatory bowel disease, the method comprising administering the GLP-2 peptibody just before surgery, during surgery, or within a period of time after surgery. In another embodiment, the GLP-2 peptibody is for use in the manufacture of a medicament for treating short bowel syndrome in a patient without inflammatory bowel disease. The medicament may be administered just before surgery, during surgery, or within a period of time after surgery.

In one aspect is provided a method of increasing the crypt depth of a patient having short bowel syndrome and reduced crypt depth as compared to a normal healthy individual. The patient receives an amount of parenteral nutrition each week or is expected to receive an amount of parenteral nutrition each week after surgery, e.g., resection of the small intestine. The patient also presents with colon-in-continuity with remnant small intestine. The method comprises administering h(Gly2)GLP-2 and/or a GLP-2 peptibody to the patient just before surgery, during surgery, or within a period of time after surgery. A dosing regimen is used that is effective to increase the crypt depth of the patient. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of increasing the crypt depth of a patient having short bowel syndrome and reduced crypt depth as compared to a normal healthy individual, the method comprising administering the GLP-2 peptibody just before surgery, during surgery, or within a period of time after surgery. In another embodiment, the GLP-2 peptibody is for use in the manufacture of a medicament for increasing the crypt depth of a patient having short bowel syndrome and reduced crypt depth as compared to a normal healthy individual. The medicament may be administered just before surgery, during surgery, or within a period of time after surgery.

In one aspect is provided a method of increasing the number of mitotic figures per 100 crypt epithelial cells of a patient having short bowel syndrome and reduced mitotic figures per 100 crypt epithelial cells as compared to a normal healthy individual. The patient receives an amount of parenteral nutrition each week or is expected to receive an amount of parenteral nutrition each week after surgery, e.g., resection of the small intestine. The patient also presents with colon-in-continuity with remnant small intestine. The method comprises administering h(Gly2)GLP-2, a GLP-2 analog and/or a GLP-2 peptibody to the patient just before surgery, during surgery, or within a period of time after surgery, using a dosing regimen effective to increase the number of mitotic figures per 100 crypt epithelial cells of the patient. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of increasing the number of mitotic figures per 100 crypt epithelial cells of a patient having short bowel syndrome and reduced mitotic figures per 100 crypt epithelial cells as compared to a normal healthy individual, the method comprising administering the GLP-2 peptibody just before surgery, during surgery, or within a period of time after surgery. In another embodiment, the GLP-2 peptibody is for use in the manufacture of a medicament for increasing the number of mitotic figures per 100 crypt epithelial cells of a patient having short bowel syndrome and reduced mitotic figures per 100 crypt epithelial cells as compared to a normal healthy individual.

Several physiological mechanisms may account for the positive effects seen on intestinal absorption with teduglutide treatment. SBS patients with end-jejunostomy, who have limited or no endogenous meal-stimulated GLP-2 secretion, often suffer from gastric hypersecretion and rapid gastric emptying, at least initially after enterectomy. GLP-2 has been shown to diminish gastric acid secretion in sham-fed healthy humans and prolong gastric emptying in SBS patients. Administration of h(Gly2)GLP-2, a GLP-2 analog and/or a GLP-2 peptibody may also diminish gastric acid secretion and prolong gastric emptying, as well as restore the physiological feedback (previously described as the ileal brake mechanism). Supraphysiological doses of h(Gly2) GLP-2, a GLP-2 analog or a GLP-2 peptibody may produce locally high concentrations that suppress gastric secretion and induce small intestine growth. Regardless of the exact physiological mechanism, increases in intestinal absorption in relation to treatments that improve intestinal adaptation would preferably be converted into positive effects regarding body weight or composition, hydration, physical activity, and ultimately, quality of life.

In one aspect is provided a method of restoring at least a portion of the ileal brake mechanism of a patient having short bowel syndrome and reduced or absent ileal brake mechanism. The patient receives an amount of parenteral nutrition each week or is expected to receive an amount of parenteral nutrition each week after surgery, e.g., resection of the small intestine. The patient also presents with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to restore at least a portion of the ileal brake mechanism of the patient. In some embodiments, the GLP-2 peptibody comprises the sequence of any of SEQ ID NOS: 2-16. In some embodiments, the GLP-2 peptibody comprises the sequence of SEQ ID NO: 4.

In one embodiment, the GLP-2 peptibody is for use in a method of restoring at least a portion of the ileal brake mechanism of a patient having short bowel syndrome and reduced or absent ileal brake mechanism, the method comprising administering the GLP-2 peptibody just before surgery, during surgery, or within a period of time after surgery. In another embodiment, the GLP-2 peptibody is for use in the manufacture of a medicament for restoring at least a portion of the ileal brake mechanism of a patient having short bowel syndrome and reduced or absent ileal brake mechanism. The medicament may be administered just before surgery, during surgery, or within a period of time after surgery.

In one aspect is provided a method of reducing gastric hypersecretion of a patient having short bowel syndrome and gastric hypersecretion. The patient receives an amount of parenteral nutrition each week or is expected to receive an amount of parenteral nutrition each week after surgery, e.g., resection of the small intestine. The patient also presents with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to reduce the gastric hypersecretion. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of reducing gastric hypersecretion of a patient having short bowel syndrome and gastric hypersecretion, the method comprising administering the GLP-2 peptibody just before surgery, during surgery, or within a period of time after surgery. In another embodiment, the GLP-2 peptibody is for use in the manufacture of a medicament for reducing gastric hypersecretion of a patient having short bowel syndrome and gastric hypersecretion. The medicament may be administered just before surgery, during surgery, or within a period of time after surgery.

In one aspect is provided a method of reducing rapid gastric emptying of a patient having short bowel syndrome and rapid gastric emptying. The patient receives an amount of parenteral nutrition each week or is expected to receive an amount of parenteral nutrition each week after surgery, e.g., resection of the small intestine. The patient also presents with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to reduce the speed of gastric emptying. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of reducing rapid gastric emptying of a patient having short bowel syndrome and rapid gastric emptying, the method comprising administering the GLP-2 peptibody just before surgery, during surgery, or within a period of time after surgery. In another embodiment, the GLP-2 peptibody is for use in the manufacture of a medicament for reducing rapid gastric emptying of a patient having short bowel syndrome and rapid gastric emptying. The medicament may be administered just before surgery, during surgery, or within a period of time after surgery.

In one aspect is provided a method of reducing or suppressing gastric secretion of a patient having short bowel syndrome. The patient receives an amount of parenteral nutrition each week or is expected to receive an amount of parenteral nutrition each week after surgery, e.g., resection of the small intestine. The patient also presents with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to reduce or suppress gastric secretion. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of reducing or suppressing gastric secretion of a patient having short bowel syndrome, the method comprising administering the GLP-2 peptibody just before surgery, during surgery, or within a period of time after surgery. In another embodiment, the GLP-2 peptibody is for use in the manufacture of a medicament for reducing or suppressing gastric secretion of a patient having short bowel syndrome. The medicament may be administered just before surgery, during surgery, or within a period of time after surgery.

In one aspect is provided a method of inducing small intestine growth of a patient having short bowel syndrome. The patient receives an amount of parenteral nutrition each week or is expected to receive an amount of parenteral nutrition each week after surgery, e.g., resection of the small intestine. The patient also presents with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to induce small intestine growth. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method for inducing small intestine growth of a patient having short bowel syndrome, the method comprising administering the GLP-2 peptibody just before surgery, during surgery, or within a period of time after surgery. In another embodiment, the GLP-2 peptibody is for use in the manufacture of a medicament for inducing small intestine growth of a patient having short bowel syndrome. The medicament may be administered just before surgery, during surgery, or within a period of time after surgery.

In one aspect is provided a method of up-regulating protein transport of a patient having short bowel syndrome. The patient receives an amount of parenteral nutrition each week or is expected to receive an amount of parenteral nutrition each week after surgery, e.g., resection of the small intestine. The patient also presents with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to upregulate the protein transport in the patient. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of up-regulating protein transport of a patient having short bowel syndrome, the method comprising administering the GLP-2 peptibody just before surgery, during surgery, or within a period of time after surgery. In another embodiment, the GLP-2 peptibody is for use in the manufacture of a medicament for up-regulating protein transport of a patient having short bowel syndrome. The medicament may be administered just before surgery, during surgery, or within a period of time after surgery.

In one aspect is provided a method of reducing occurrence of dehydration of a patient having short bowel syndrome, or who is expected to have short bowel syndrome, e.g., intestinal resection. The method comprises administering h(Gly2)GLP-2, a GLP-2 analog and/or a GLP-2 peptibody to the patient just before surgery, during surgery, or within a period of time after surgery. A dosing regimen is used that is effective to reduce the likelihood of dehydration occurrence in the patient. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of reducing occurrence of dehydration of a patient having short bowel syndrome, the method comprising administering the GLP-2 peptibody just before surgery, during surgery, or within a period of time after surgery. In another embodiment, the GLP-2 peptibody is for use in the manufacture of a medicament for reducing occurrence of dehydration of a patient having short bowel syndrome. The medicament may be administered just before surgery, during surgery, or within a period of time after surgery.

In one aspect is provided a method of reducing occurrence of renal insufficiency of a patient having short bowel syndrome, or who is expected to have short bowel syndrome, e.g., intestinal resection. The method comprises administering h(Gly2)GLP-2, a GLP-2 analog and/or a GLP-2 peptibody to the patient just before surgery, during surgery, or within a period of time after surgery. A dosing regimen is used that is effective to reduce the likelihood of renal insufficiency occurrence in the patient. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of reducing occurrence of renal insufficiency of a patient having short bowel syndrome, the method comprising administering the GLP-2 peptibody just before surgery, during surgery, or within a period of time after surgery. In another embodiment, the GLP-2 peptibody is for use in the manufacture of a medicament for reducing occurrence of renal insufficiency of a patient having short bowel syndrome. The medicament may be administered just before surgery, during surgery, or within a period of time after surgery.

In one aspect is provided a method of reducing occurrence of kidney stones in a patient having short bowel syndrome, or who is expected to have short bowel syndrome after surgery, e.g., intestinal resection. The method comprises administering h(Gly2)GLP-2, a GLP-2 analog and/or a GLP-2 peptibody to the patient just before surgery, during surgery, or within a period of time after surgery. A dosing regimen is used that is effective to reduce the likelihood of kidney stone occurrence in the patient. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of reducing occurrence of kidney stones in a patient having short bowel syndrome, the method comprising administering the GLP-2 peptibody just before surgery, during surgery, or within a period of time after surgery. In another embodiment, the GLP-2 peptibody is for use in the manufacture of a medicament for reducing occurrence of kidney stones in a patient having short bowel syndrome. The medicament may be administered just before surgery, during surgery, or within a period of time after surgery.

In one aspect is provided a method for treating a patient with short bowel syndrome presenting with colon-in-continuity with remnant small intestine, or expected to have short bowel syndrome presenting with colon-in-continuity with remnant small intestine post-surgery, e.g., intestinal resection. The method comprises administering h(Gly2)GLP-2, a GLP-2 analog and/or a GLP-2 peptibody to the patient just before surgery, during surgery, or within a period of time after surgery. A dosing regimen is used that is effective to enhance intestinal absorption by the patient. In some embodiments, the GLP-2 peptibody comprises the sequence of any of SEQ ID NOS: 2-16. In some embodiments, the GLP-2 peptibody comprises the sequence of SEQ ID NO: 4. In another embodiment, the GLP-2 peptibody is for use in a method of treating short bowel syndrome in a patient presenting with colon-in-continuity with remnant small intestine, the method comprising administering the GLP-2 peptibody just before surgery, during surgery, or within a period of time after surgery. In another embodiment, the GLP-2 peptibody is for use in the manufacture of a medicament for treating short bowel syndrome in a patient presenting with colon-in-continuity with remnant small intestine. The medicament may be administered just before surgery, during surgery, or within a period of time after surgery.

In one aspect is provided a method for treating a patient with short bowel syndrome presenting with colon-in-continuity with remnant small intestine, or expected to have short bowel syndrome presenting with colon-in-continuity with remnant small intestine post-surgery, e.g., intestinal resection. The method comprises administering to the patient h(Gly2)GLP-2, a GLP-2 analog and/or a GLP-2 peptibody just before surgery, during surgery, or within a period of time after surgery. A dosing regimen is used that is effective to enhance intestinal absorption by the patient. The h(Gly2) GLP-2 is administered intravenously at a daily dose of 0.04 to 0.06 mg/kg body weight, e.g., 0.05 mg/kg body weight. The GLP-2 peptibody is administered at a dose of from 30 to 150 µg/kg by subcutaneous injection into the abdomen, thigh, or arm of the patient. The administration may be daily. Dose adjustments can be made on an individual basis based on achievement and maintenance of therapeutic goals. In some embodiments, the GLP-2 peptibody comprises the sequence of any of SEQ ID NOS: 2-16. In some embodiments, the GLP-2 peptibody comprises the sequence of SEQ ID NO: 4.

In one aspect is provided a method for treating a patient with short bowel syndrome presenting with colon-in-continuity with remnant small intestine, or expected to have short bowel syndrome presenting with colon-in-continuity with remnant small intestine post-surgery, e.g., intestinal resection. The method comprises administering h(Gly2)GLP-2, a GLP-2 analog and/or a GLP-2 peptibody to the patient just before surgery, during surgery, or within a period of time after surgery. A dosing regimen is used that is effective to enhance intestinal absorption by the patient. The h(Gly2) GLP-2 is administered intravenously at a daily dose of 0.04 to 0.06 mg/kg body weight, e.g., 0.05 mg/kg body weight. The GLP-2 peptibody is administered at a dose of from 30 to 150 µg/kg by subcutaneous injection into the abdomen, thigh, or arm of the patient. The administration may be daily. Dose adjustments can be made on an individual basis based on achievement and maintenance of therapeutic goals. In some embodiments, the GLP-2 peptibody comprises the sequence of any of SEQ ID NOS: 2-16. In some embodiments, the GLP-2 peptibody comprises the sequence of SEQ ID NO: 4.

In one aspect is provided a method for treating a patient with short bowel syndrome who is dependent on parenteral nutrition and is presenting with colon-in-continuity with remnant small intestine, or expected to have short bowel syndrome presenting with colon-in-continuity with remnant small intestine post-surgery, e.g., intestinal resection. The method comprises administering h(Gly2)GLP-2, a GLP-2 analog and/or a GLP-2 peptibody to the patient just before surgery, during surgery, or within a period of time after surgery. A dosing regimen is used that is effective to enhance intestinal absorption by the patient. Dose adjustments can be made on an individual basis based on achievement and maintenance of therapeutic goals. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of treating short bowel syndrome in a patient who is dependent on parenteral nutrition and is presenting with colon-in-continuity with remnant small intestine, the method comprising administering the GLP-2 peptibody just before surgery, during surgery, or within a period of time after surgery. In another embodiment, the GLP-2 peptibody is for use in the manufacture of a medicament for treating short bowel syndrome in a patient who is dependent on parenteral nutrition and is presenting with colon-in-continuity with remnant small intestine. The medicament may be administered just before surgery, during surgery, or within a period of time after surgery.

In one aspect is provided a method of increasing the villus height of a patient having, or expected to have post-surgery, e.g., intestinal resection, short bowel syndrome and reduced villus height as compared to a normal healthy individual, who receives an amount of parenteral nutrition each week, and who presents with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to increase the villus height of the patient. Dose adjustments can be made on an individual basis based on achievement and maintenance of therapeutic goals. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of treating short bowel syndrome in a patient who receives an amount of parenteral nutrition each week, the method comprising administering the GLP-2 peptibody just before surgery, during surgery, or within a period of time after surgery. In another embodiment, the GLP-2 peptibody is for use in the manufacture of a medicament for treating short bowel syndrome in a patient who receives an amount of parenteral nutrition each week. The medicament may be administered just before surgery, during surgery, or within a period of time after surgery.

In the various embodiments and aspects described herein, the effects of h(Gly2)GLP-2 and GLP-2 peptibodies on stimulating mucosal growth in the small intestine may be helpful to reduce the amount of total parenteral nutrition (TPN) needed immediately after surgery. As with GLP-2, h(Gly2)GLP-2 and GLP-2 peptibodies can increase villus height, crypt depth and overall intestinal mucosal surface area. The longer half life of h(Gly2)GLP-2 and GLP-2 peptibodies as compared to GLP-2 may lead to a more quick and sustained increase. Thus, even after a surgical resection of the small intestine, the overall surface area increase could compensate for losses in the overall length of the small intestine.

Figure 1:
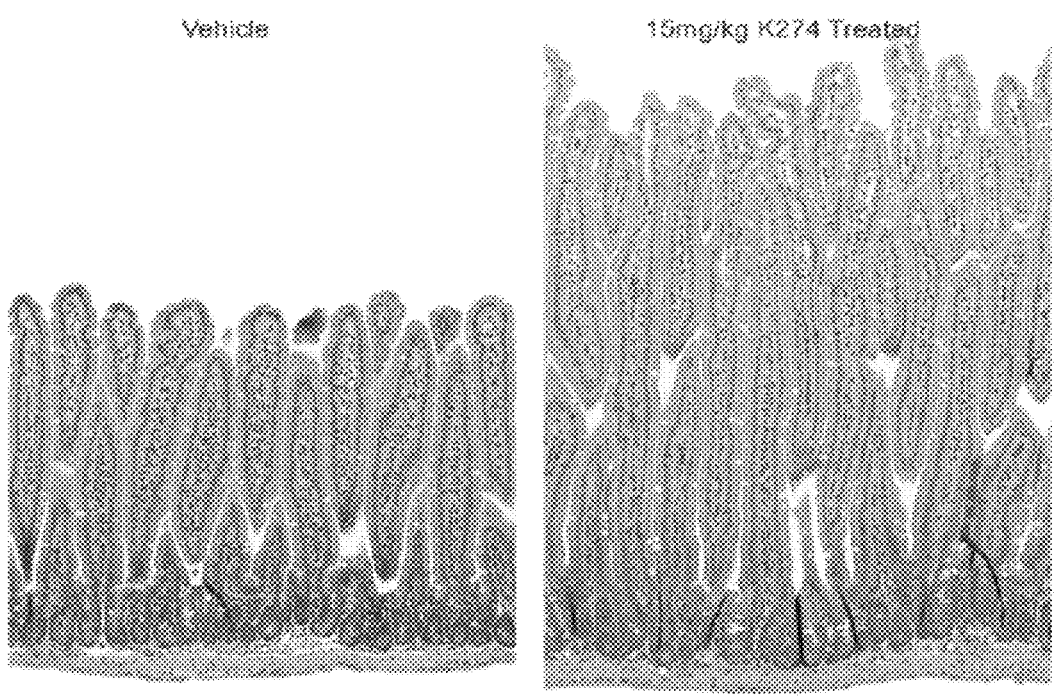
FIG. 1 shows the crypts and villi of the small intestine without treatment (left panel), with and with GLP-2 peptibody K274 treatment (right panel). The GLP-2 peptibody K274 has the amino acid sequence set forth in SEQ ID NO: 4.
Figure 2:
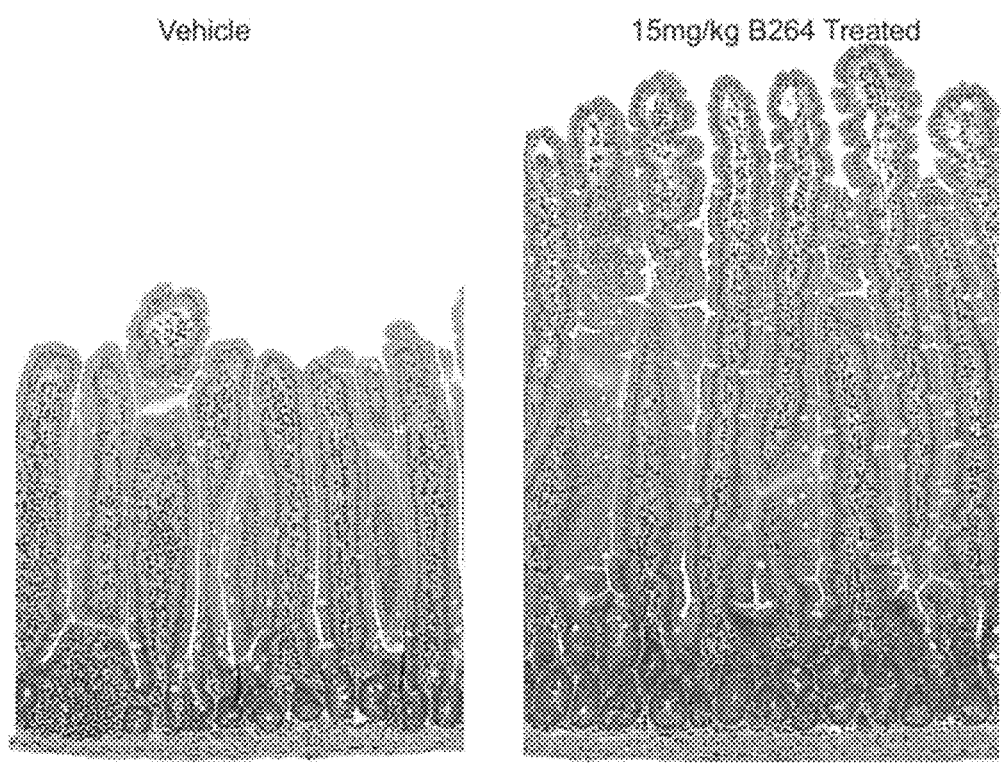
FIG. 2 shows the crypts and villi of the small intestine without treatment (left panel), with and with GLP-2 peptibody B264 treatment (right panel). The GLP-2 peptibody B264 has the amino acid sequence set forth in SEQ ID NO: 2.
Figure 3:
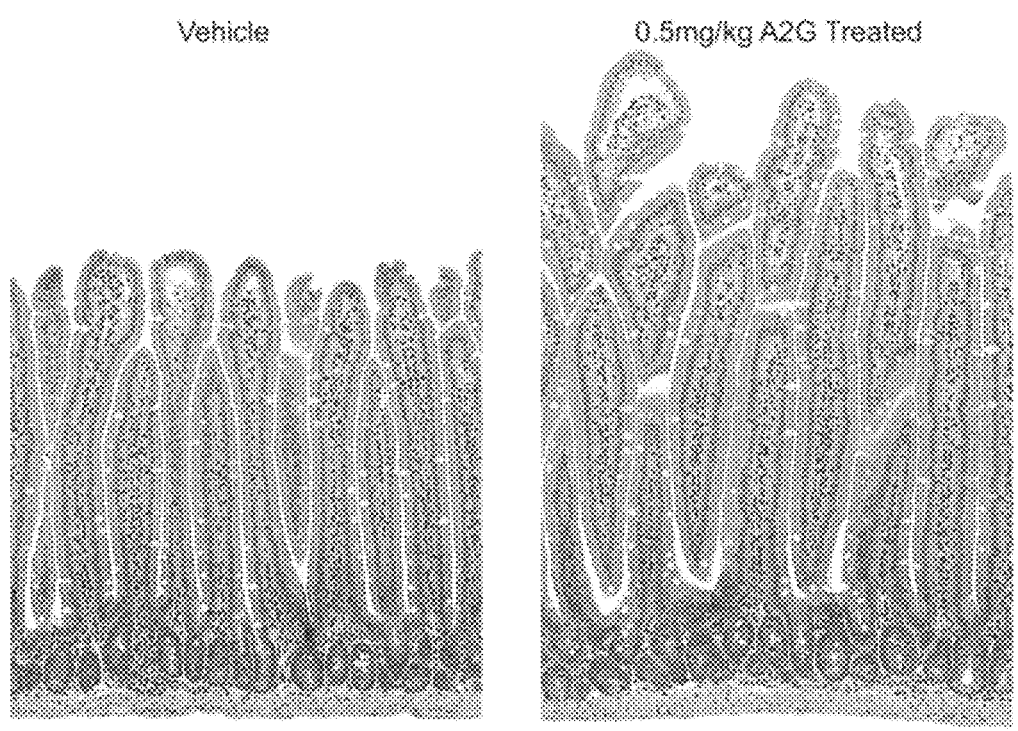
FIG. 3 shows the crypts and villi of the small intestine without treatment (left panel), with and with GLP-2[A2G], an h(Gly2)GLP-2 (right panel).

Total parenteral nutrition (TPN) has been described by Lei et al. as blunting the villi in the small intestine, or otherwise decreasing the villus height. See, Lei, Q. et al., Nutrients, 2016, 8:33. Administration of h(Gly2)GLP-2 or a GLP-2 peptibody may prevent the villi from becoming blunted, particularly if these are administered to the patient just before surgery, during surgery, or within a period of time after surgery. See, e.g., FIGS. 1-3 in which administration of GLP-2 peptibody B264, GLP-2 peptibody K274 or h(Gly2)GLP-2 increased villus height. By preventing the villi from becoming blunted, absorption across the small intestine may be maximized after a surgery involving removing a portion of the small intestine followed by resection.

In one aspect is provided a method of treating a patient having short bowel syndrome with non-malignant disease, who receives an amount of parenteral nutrition each week, and who presents with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to increase wet weight absorption compared to a baseline wet weight absorption by the patient. Dose adjustments can be made on an individual basis based on achievement and maintenance of therapeutic goals. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of treating short bowel syndrome with non-malignant disease in a patient who receives an amount of parenteral nutrition each week, the method comprising administering the GLP-2 peptibody just before surgery, during surgery, or within a period of time after surgery. In another embodiment, the GLP-2 peptibody is for use in the manufacture of a medicament for treating short bowel syndrome with non-malignant disease in a patient who receives an amount of parenteral nutrition each week. The medicament may be administered just before surgery, during surgery, or within a period of time after surgery.

In one aspect is provided a method of treating a patient having short bowel syndrome with Crohn's disease. The patient receives an amount of parenteral nutrition each week. The patient also presents with colon-in-continuity with remnant small intestine. Alternatively, the patient may not have short bowel syndrome but is expected post-surgery to have short bowel syndrome with Crohn's disease, receive an amount of parenteral nutrition each week, and present with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to reduce increase wet weight absorption compared to a baseline wet weight absorption by the patient. Dose adjustments can be made on an individual basis based on achievement and maintenance of therapeutic goals. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of treating short bowel syndrome with Crohn's disease, the method comprising administering the GLP-2 peptibody just before surgery, during surgery, or within a period of time after surgery. In another embodiment, the GLP-2 peptibody is for use in the manufacture of a medicament for treating short bowel syndrome with Crohn's disease. The medicament may be administered just before surgery, during surgery, or within a period of time after surgery.

In one aspect is provided a method of treating a patient having short bowel syndrome with mesenteric infarction. The patient receives an amount of parenteral nutrition each week and presents with colon-in-continuity with remnant small intestine. Alternatively, the patient may not have short bowel syndrome but is expected post-surgery to have short bowel syndrome with mesenteric infarction, receive an amount of parenteral nutrition each week, and present with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to increase wet weight absorption compared to a baseline wet weight absorption by the patient. Dose adjustments can be made on an individual basis based on achievement and maintenance of therapeutic goals. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of treating short bowel syndrome with mesenteric infarction, the method comprising administering the GLP-2 peptibody just before surgery, during surgery, or within a period of time after surgery. In another embodiment, the GLP-2 peptibody is for use in the manufacture of a medicament for treating short bowel syndrome with mesenteric infarction. The medicament may be administered just before surgery, during surgery, or within a period of time after surgery.

In one aspect is provided a method of treating a patient having short bowel syndrome with, or secondary to, volvulus. The patient receives an amount of parenteral nutrition each week and presents with colon-in-continuity with remnant small intestine. Alternatively, the patient may not have short bowel syndrome but is expected post-surgery, e.g., intestinal resection to treat volvulus, to have short bowel syndrome, receive an amount of parenteral nutrition each week, and present with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to increase wet weight absorption compared to a baseline wet weight absorption by the patient. Dose adjustments can be made on an individual basis based on achievement and maintenance of therapeutic goals. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of treating short bowel syndrome with, or secondary to, volvulus, the method comprising administering the GLP-2 peptibody just before surgery, during surgery, or within a period of time after surgery. In another embodiment, the GLP-2 peptibody is for use in the manufacture of a medicament for treating short bowel syndrome with, or secondary to, volvulus. The medicament may be administered just before surgery, during surgery, or within a period of time after surgery.

In one aspect is provided a method of treating a patient having short bowel syndrome secondary to congenital intestinal abnormalities. The patient receives an amount of parenteral nutrition each week and presents with colon-in-continuity with remnant small intestine. Alternatively, the patient may not have short bowel syndrome but is expected to have post-surgery, e.g., intestinal resection, short bowel syndrome secondary to congenital intestinal abnormalities, receive an amount of parenteral nutrition each week, and present with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to increase wet weight absorption compared to a baseline wet weight absorption by the patient. Dose adjustments can be made on an individual basis based on achievement and maintenance of therapeutic goals. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of treating short bowel syndrome secondary to congenital intestinal abnormalities, the method comprising administering the GLP-2 peptibody just before surgery, during surgery, or within a period of time after surgery. In another embodiment, the GLP-2 peptibody is for use in the manufacture of a medicament for treating short bowel syndrome secondary to congenital intestinal abnormalities. The medicament may be administered just before surgery, during surgery, or within a period of time after surgery.

In one aspect is provided a method of treating a patient having short bowel syndrome without inflammatory bowel disease. The patient receives an amount of parenteral nutrition each week and presents with colon-in-continuity with remnant small intestine. Alternatively, the patient may not have short bowel syndrome but is expected to have post-surgery, e.g., intestinal resection, short bowel syndrome without inflammatory bowel disease, receive an amount of parenteral nutrition each week, and present with colon-in-continuity with remnant small intestine. The method comprises administering h(Gly2)GLP-2 and/or a GLP-2 peptibody to the patient just before surgery, during surgery, or within a period of time after surgery. A dosing regimen is used that is effective to reduce or eliminate the weekly amount of parenteral nutrition received by the patient. Dose adjustments can be made on an individual basis based on achievement and maintenance of therapeutic goals. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of treating short bowel syndrome without inflammatory bowel disease, the method comprising administering the GLP-2 peptibody just before surgery, during surgery, or within a period of time after surgery. In another embodiment, the GLP-2 peptibody is for use in the manufacture of a medicament for treating short bowel syndrome without inflammatory bowel disease. The medicament may be administered just before surgery, during surgery, or within a period of time after surgery.

In one aspect is provided a method of treating a patient having short bowel syndrome secondary to multiple strictures due to adhesions or radiation, and who receives an amount of parenteral nutrition each week. Alternatively, the patient may not have short bowel syndrome but is expected to have post-surgery, e.g., intestinal resection, short bowel syndrome secondary to multiple strictures due to adhesions or radiation, and receive an amount of parenteral nutrition each week. The method comprises administering a GLP-2 receptor agonist, e.g., h(Gly2)GLP-2, a GLP-2 analog and/or a GLP-2 peptibody, to the patient just before surgery, during surgery, or within a period of time after surgery. A dosing regimen is used that is effective to increase wet weight absorption compared to a baseline wet weight absorption by the patient. Dose adjustments can be made on an individual basis based on achievement and maintenance of therapeutic goals. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of treating short bowel syndrome secondary to multiple strictures due to adhesions or radiation in a patient who receives an amount of parenteral nutrition each week, the method comprising administering the GLP-2 peptibody just before surgery, during surgery, or within a period of time after surgery. In another embodiment, the GLP-2 peptibody is for use in the manufacture of a medicament for treating short bowel syndrome secondary to multiple strictures due to adhesions or radiation in a patient who receives an amount of parenteral nutrition each week. The medicament may be administered just before surgery, during surgery, or within a period of time after surgery.

In one aspect is provided a method of treating a patient having short bowel syndrome secondary to vascular ischemia. The patient receives an amount of parenteral nutrition each week, and presents with colon-in-continuity with remnant small intestine. Alternatively, the patient may not have short bowel syndrome but is expected to have post-surgery, e.g., intestinal resection, short bowel syndrome secondary to vascular ischemia, receive an amount of parenteral nutrition each week, and present with colon-in-continuity with remnant small intestine. The method comprises administering a GLP-2 receptor agonist, e.g., h(Gly2)GLP-2, a GLP-2 analog and/or a GLP-2 peptibody, to the patient just before surgery, during surgery, or within a period of time after surgery. A dosing regimen is used that is effective to increase wet weight absorption compared to a baseline wet weight absorption by the patient. Dose adjustments can be made on an individual basis based on achievement and maintenance of therapeutic goals. In some embodiments, the GLP-2 peptibody comprises the sequence of any of SEQ ID NOS: 2-16. In some embodiments, the GLP-2 peptibody comprises the sequence of SEQ ID NO: 4. In another embodiment, the GLP-2 peptibody is for use in a method of treating short bowel syndrome secondary to vascular ischemia in a patient who receives an amount of parenteral nutrition each week, the method comprising administering the GLP-2 peptibody just before surgery, during surgery, or within a period of time after surgery. In another embodiment, the GLP-2 peptibody is for use in the manufacture of a medicament for treating short bowel syndrome secondary to vascular ischemia in a patient who receives an amount of parenteral nutrition each week. The medicament may be administered just before surgery, during surgery, or within a period of time after surgery.

Such GLP-2 receptor agonists are characterized as molecules that bind with, preferably selectively, and stimulate the human GLP-2 receptor, as reported by Monroe et al. in U.S. Pat. No. 6,077,949 issued Jun. 20, 2000, incorporated herein by reference. Briefly, GLP-2 receptor agonists are revealed as agents that trigger production of, or trigger an elevation in the level of, a second messenger coupled to the human GLP-2 receptor, when exposed to a host cell that produces that receptor naturally or is transfected with DNA encoding that receptor.

In one aspect is provided a method of treating a patient having short bowel syndrome with at least 25% colon-in-continuity with remnant small intestine and who receives an amount of parenteral nutrition each week. Alternatively, the patient may not have short bowel syndrome but is expected to have post-surgery, e.g., intestinal resection, short bowel syndrome with at least 25% colon-in-continuity with remnant small intestine and receive an amount of parenteral nutrition each week. The method comprises administering a GLP-2 receptor agonist, e.g., h(Gly2)GLP-2, a GLP-2 analog and/or a GLP-2 peptibody, to the patient just before surgery, during surgery, or within a period of time after surgery. A dosing regimen is used that is effective to increase wet weight absorption compared to a baseline wet weight absorption by the patient. Dose adjustments can be made on an individual basis based on achievement and maintenance of therapeutic goals. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of treating short bowel syndrome with at least 25% colon-in-continuity with remnant small intestine in a patient who receives an amount of parenteral nutrition each week, the method comprising administering the GLP-2 peptibody just before surgery, during surgery, or within a period of time after surgery. In another embodiment, the GLP-2 peptibody is for use in the manufacture of a medicament for treating short bowel syndrome with at least 25% colon-in-continuity with remnant small intestine in a patient who receives an amount of parenteral nutrition each week.

In another aspect is provided a method of treating a patient having short bowel syndrome with elevated (as compared to a normal healthy individual) basal levels of endogenous GLP-2. The patient receives an amount of parenteral nutrition each week and presents with colon-in-continuity with remnant small intestine. Alternatively, the patient may not have short bowel syndrome but is expected to have post-surgery, e.g., intestinal resection, short bowel syndrome with elevated (as compared to a normal healthy individual) basal levels of endogenous GLP-2, receive an amount of parenteral nutrition each week, and present with colon-in-continuity with remnant small intestine. The method comprises administering a GLP-2 receptor agonist, e.g., h(Gly2)GLP-2, a GLP-2 analog and/or a GLP-2 peptibody, to the patient just before surgery, during surgery, or within a period of time after surgery. A dosing regimen is used that is effective to increase wet weight absorption compared to a baseline wet weight absorption by the patient. Dose adjustments can be made on an individual basis based on achievement and maintenance of therapeutic goals. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of treating short bowel syndrome in a patient with elevated (as compared to a normal healthy individual) basal levels of endogenous GLP-2, the method comprising administering the GLP-2 peptibody just before surgery, during surgery, or within a period of time after surgery. In another embodiment, the GLP-2 peptibody is for use in the manufacture of a medicament for treating short bowel syndrome in a patient with elevated (as compared to a normal healthy individual) basal levels of endogenous GLP- 2. The medicament may be administered just before surgery, during surgery, or within a period of time after surgery.

In another aspect is provided a method for treating a patient having short bowel syndrome with elevated (as compared to a normal healthy individual) basal levels of endogenous GLP-2 and who is dependent on parenteral nutrition. Alternatively, the patient may not have short bowel syndrome but is expected to have post-surgery, e.g., intestinal resection, short bowel syndrome with elevated (as compared to a normal healthy individual) basal levels of endogenous GLP-2 and be dependent on parenteral nutrition. The method comprises administering a GLP-2 receptor agonist, e.g., h(Gly2)GLP-2, a GLP-2 analog and/or a GLP-2 peptibody, to the patient just before surgery, during surgery, or within a period of time after surgery. A dosing regimen is used that is effective to enhance intestinal absorption by the patient. Dose adjustments can be made on an individual basis based on achievement and maintenance of therapeutic goals. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of treating short bowel syndrome in a patient with elevated (as compared to a normal healthy individual) basal levels of endogenous GLP-2 and who is dependent on parenteral nutrition, the method comprising administering the GLP-2 peptibody just before surgery, during surgery, or within a period of time after surgery. In another embodiment, the GLP-2 peptibody is for use in the manufacture of a medicament for treating short bowel syndrome in a patient with elevated (as compared to a normal healthy individual) basal levels of endogenous GLP-2 and who is dependent on parenteral nutrition. The medicament may be administered just before surgery, during surgery, or within a period of time after surgery.

In one aspect is provided a method of treating a patient having short bowel syndrome with equal or elevated (as compared to a normal healthy individual) meal stimulated levels of endogenous GLP-2. The patient receives an amount of parenteral nutrition each week and presents with colon-in-continuity with remnant small intestine. Alternatively, the patient may not have short bowel syndrome but is expected to have post-surgery, e.g., intestinal resection, short bowel syndrome with equal or elevated (as compared to a normal healthy individual) meal stimulated levels of endogenous GLP-2, receive an amount of parenteral nutrition each week, and present with colon-in-continuity with remnant small intestine. The method comprises administering a GLP-2 receptor agonist, e.g., h(Gly2)GLP-2, a GLP-2 analog and/or a GLP-2 peptibody, to the patient just before surgery, during surgery, or within a period of time after surgery. A dosing regimen is used that is effective to increase wet weight absorption compared to a baseline wet weight absorption by the patient. Dose adjustments can be made on an individual basis based on achievement and maintenance of therapeutic goals. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of treating short bowel syndrome in a patient with equal or elevated (as compared to a normal healthy individual) meal stimulated levels of endogenous GLP-2 and who is dependent on parenteral nutrition, the method comprising administering the GLP-2 peptibody just before surgery, during surgery, or within a period of time after surgery. In another embodiment, the GLP-2 peptibody is for use in the manufacture of a medicament for treating short bowel syndrome in a patient with equal or elevated (as compared to a normal healthy individual) meal stimulated levels of endogenous GLP-2 and who is dependent on parenteral nutrition. The medicament may be administered just before surgery, during surgery, or within a period of time after surgery.

In another aspect is provided a method of treating a patient having short bowel syndrome with colon-in-continuity with remnant small intestine ranging from about 25 cm to about 200 cm and who receives an amount of parenteral nutrition each week. Alternatively, the patient may not have short bowel syndrome but is expected to have post-surgery, e.g., intestinal resection, short bowel syndrome with colon-in-continuity with remnant small intestine ranging from about 25 cm to about 200 cm and who receives an amount of parenteral nutrition each week. The method comprises administering a GLP-2 receptor agonist to the patient just before surgery, during surgery, or within a period of time after surgery. A dosing regimen is used that is effective to increase wet weight absorption compared to a baseline wet weight absorption by the patient. The GLP-2 agonist is selected from the group consisting of GLP-2 peptide and a GLP-2 analog. The GLP-2 agonist may be h(Gly2)GLP-2. The GLP-2 agonist may be a GLP-2 peptibody. Dose adjustments can be made on an individual basis based on achievement and maintenance of therapeutic goals. In some embodiments, the GLP-2 peptibody comprises the sequence of any of SEQ ID NOS: 2-16. In some embodiments, the GLP-2 peptibody comprises the sequence of SEQ ID NO: 4. The GLP-2 agonist may be a combination of h(Gly2)GLP-2 and a GLP-2 peptibody. In one embodiment, the GLP-2 peptibody is for use in a method of treating short bowel syndrome in a patient presenting with colon-in-continuity with remnant small intestine ranging from about 25 cm to about 200 cm and who receives an amount of parenteral nutrition each week, the method comprising administering the GLP-2 peptibody just before surgery, during surgery, or within a period of time after surgery. In another embodiment, the GLP-2 peptibody is for use in the manufacture of a medicament for treating short bowel syndrome in a patient presenting with colon-in-continuity with remnant small intestine ranging from about 25 cm to about 200 cm and who receives an amount of parenteral nutrition each week. The medicament may be administered just before surgery, during surgery, or within a period of time after surgery.

In one aspect is provided a method of treating a patient having short bowel syndrome with colon-in-continuity and at least about 50 cm of remnant small intestine and who receives an amount of parenteral nutrition each week. The method comprises administering h(Gly2)GLP-2, a GLP-2 analog and/or a GLP-2 peptibody to the patient just before surgery, during surgery, or within a period of time after surgery. A dosing regimen is used that is effective to reduce increase wet weight absorption compared to a baseline wet weight absorption by the patient. Dose adjustments can be made on an individual basis based on achievement and maintenance of therapeutic goals. In some embodiments, the GLP-2 peptibody comprises the sequence of any of SEQ ID NOS: 2-16. In some embodiments, the GLP-2 peptibody comprises the sequence of SEQ ID NO: 4. In another embodiment, the GLP-2 peptibody is for use in a method of treating short bowel syndrome in a patient presenting with at least about 50 cm of remnant small intestine and who receives an amount of parenteral nutrition each week, the method comprising administering the GLP-2 peptibody just before surgery, during surgery, or within a period of time after surgery. In another embodiment, the GLP-2 peptibody is for use in the manufacture of a medicament for treating short bowel syndrome in a patient presenting with at least about 50 cm of remnant small intestine and who receives an amount of parenteral nutrition each week. The medicament may be administered just before surgery, during surgery, or within a period of time after surgery.

In another aspect is provided a method of treating a patient having short bowel syndrome without inflammatory bowel disease. The patient receives an amount of parenteral nutrition each week and presents with colon-in-continuity with remnant small intestine. Alternatively, the patient may not have short bowel syndrome but is expected to have short bowel syndrome without inflammatory bowel disease, receive an amount of parenteral nutrition each week, and present with colon-in-continuity with remnant small intestine. The method comprises administering h(Gly2)GLP-2, a GLP-2 analog and/or a GLP-2 peptibody to the patient just before surgery, during surgery, or within a period of time after surgery. A dosing regimen is used that is effective to increase wet weight absorption compared to a baseline wet weight absorption by the patient. Dose adjustments can be made on an individual basis based on achievement and maintenance of therapeutic goals. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of treating short bowel syndrome without inflammatory bowel disease in a patient who receives an amount of parenteral nutrition each week, the method comprising administering the GLP-2 peptibody just before surgery, during surgery, or within a period of time after surgery. In another embodiment, the GLP-2 peptibody is for use in the manufacture of a medicament for treating short bowel syndrome without inflammatory bowel disease in a patient who receives an amount of parenteral nutrition each week. The medicament may be administered just before surgery, during surgery, or within a period of time after surgery.

In another aspect is provided a method for treating a patient with short bowel syndrome who is dependent on parenteral nutrition and who presents with colon-in-continuity with remnant small intestine. Alternatively, the patient may not have short bowel syndrome but is expected to have post-surgery, e.g., intestinal resection, short bowel syndrome, be dependent on parenteral nutrition and present with colon-in-continuity with remnant small intestine. The method comprises administering to the patient h(Gly2)GLP-2, a GLP-2 analog and/or a GLP-2 peptibody just before surgery, during surgery, or within a period of time after surgery. A dosing regimen is used that is effective to reduce the dependency on parenteral nutrition by the patient. Dose adjustments can be made on an individual basis based on achievement and maintenance of therapeutic goals. In some embodiments, the GLP-2 peptibody comprises the sequence of any of SEQ ID NOS: 2-16. In some embodiments, the GLP-2 peptibody comprises the sequence of SEQ ID NO: 4. In one embodiment, the GLP-2 peptibody is for use in a method of treating short bowel syndrome in a patient who is dependent on parenteral nutrition and who presents with colon-in-continuity with remnant small intestine, the method comprising administering the GLP-2 peptibody just before surgery, during surgery, or within a period of time after surgery. In another embodiment, the GLP-2 peptibody is for use in the manufacture of a medicament for treating short bowel syndrome in a patient who is dependent on parenteral nutrition and who presents with colon-in-continuity with remnant small intestine. The medicament may be administered just before surgery, during surgery, or within a period of time after surgery.

In yet another aspect is provided a method for treating a patient with short bowel syndrome who is dependent on parenteral nutrition and who presents with colon-in-continuity with remnant small intestine. Alternatively, the patient may not have short bowel syndrome but is expected to have post-surgery, e.g., intestinal resection, short bowel syndrome, to be dependent on parenteral nutrition and present with colon-in-continuity with remnant small intestine. The method comprises administering to the patient h(Gly2)GLP-2, a GLP-2 analog and/or a GLP-2 peptibody just before surgery, during surgery, or within a period of time after surgery. A dosing regimen is used that is effective to reduce the dependency on parenteral nutrition by the patient. The h(Gly2)GLP-2 is administered intravenously at a daily dose of 0.04 to 0.06 mg/kg body weight, e.g., 0.05 mg/kg body weight. Dose adjustments can be made on an individual basis based on achievement and maintenance of therapeutic goals. In some embodiments, the GLP-2 peptibody comprises the sequence of any of SEQ ID NOS: 2-16. In some embodiments, the GLP-2 peptibody comprises the sequence of SEQ ID NO: 4. The GLP-2 peptibody is administered daily at a dose of from 30 to 150 µg/kg by subcutaneous injection into the abdomen, thigh, or arm.

In one aspect is provided a method for treating an adult patient with short bowel syndrome who is dependent on parenteral nutrition and who presents with colon-in-continuity with remnant small intestine. Alternatively, the patient may not have short bowel syndrome but is expected to have post-surgery, e.g., intestinal resection, short bowel syndrome, be dependent on parenteral nutrition and present with colon-in-continuity with remnant small intestine. The method comprises administering to the patient h(Gly2)GLP-2, a GLP-2 analog and/or a GLP-2 peptibody just before surgery, during surgery, or within a period of time after surgery. A dosing regimen is used that is effective to reduce the dependency on parenteral nutrition by the patient. Dose adjustments can be made on an individual basis based on achievement and maintenance of therapeutic goals. In some embodiments, the GLP-2 peptibody comprises the sequence of any of SEQ ID NOS: 2-16. In some embodiments, the GLP-2 peptibody comprises the sequence of SEQ ID NO: 4.

In any of the above aspects and embodiments in which h(Gly2)GLP-2 and/or a GLP-2 peptibody is administered just before surgery or within a period of time after surgery, various dosing schedules may be used. Twice daily administration can be beneficial. Twice daily (every 12 hours) dosing usefully delivers about 5 to 250 µg/kg/dose. Benefits can also accrue to schedules that entail more frequent dosing or less frequent dosing. In addition, followup dosing can be undertaken. Such followup dosing can occur as part of a treatment plan for longer-term administration of h(Gly2) GLP-2, a GLP-2 analog or GLP-2 peptibody, or before such treatment plan has been prepared. Follow-up dosing usefully occurs at regular frequencies such as weekly, biweekly, every month, every three months, etc. Continued dosing usefully provides to the patient a dose efficient to maintain the benefits of increased absorptive surface area with increased intestinal absorption that arise from initial treatment, and can be effected by dosing the patient at least once within every 1-28 days, e.g., every other day, 2-3 times per week, once per week, etc. Continued or follow-up dosing can be important to preserve the medical benefits mediated by the GLP-2 receptor agonist; as noted in the examples, improvements in intestinal absorption following treatment with teduglutide for instance, can be lost rapidly, for example within four weeks following cessation of dosing.

During surgery, h(Gly2)GLP-2, a GLP-2 analog or GLP-2 peptibody may be administered by infusion or by any other route that delivers the drug to the target site on the serosal side of the intestinal tissue, such as by depot injection. If delivered by injection, the drug can be formulated as a lyophilized powder for reconstitution by the user, and as either unit or multiple doses. One formulation of teduglutide, for instance, is described in WO 01/49314 published Jul. 12, 2001, and provides a powder for reconstitution in which teduglutide is present with L-histidine, mannitol and sodium phosphate. This is usefully provided as a 3 mL glass vial containing 10 mg teduglutide, for reconstitution with 1 mL water for injection and self-administration. An alternative formulation provides 10 mg of teduglutide in a smaller volume of aqueous vehicle, such as 0.5 mL water for injection.

The patient may have short bowel syndrome with Crohn's disease, or secondary to Crohn's disease. The patient may have short bowel syndrome with mesenteric infarction, or secondary to mesenteric infarction. The patient may have short bowel syndrome with volvulus, or secondary to volvulus. The patient may have short bowel syndrome with congenital intestinal abnormalities, or secondary to congenital intestinal abnormalities. The patient may have short bowel syndrome with, or secondary to, multiple strictures due to adhesions or radiation. The patient may have short bowel syndrome with, or secondary to, vascular ischemia. The patient may have limited, but some detectable, meal-stimulated GLP-2 secretion (as compared to a normal healthy individual). The patient may have less, but some detectable, GLP-2 producing tissue (as compared to a normal healthy individual). The patient may have elevated basal levels of endogenous GLP-2 (as compared to a normal healthy individual).

The patient may have short bowel syndrome without inflammatory bowel disease. In certain embodiments, the short bowel syndrome is not secondary to inflammatory bowel disease. In certain embodiments, the patient has short bowel syndrome but does not have inflammatory bowel disease.

The patient may have at least 25% colon-in-continuity with remnant small intestine and receive an amount of parenteral nutrition each week. In some embodiments, the patient has at least 30% colon-in-continuity. In some embodiments, the patient has at least 35% colon-in-continuity. In some embodiments, the patient has at least 40% colon-in-continuity. In some embodiments, the patient has at least 45% colon-in-continuity. In some embodiments, the patient has at least 50% colon-in-continuity. In some embodiments, the patient has at least 60% colon-in-continuity. In some embodiments, the patient has at least 70% colon-in-continuity. In some embodiments, the patient has at least 80% colon-in-continuity. In some embodiments, the patient has at least 90% colon-in-continuity.

The patient may have short bowel syndrome colon-in-continuity and remnant small intestine ranging from about 25 cm to about 200 cm. The patient may have a length of small intestine ranging from about 50 to 150 cm. The patient may have at least about 50 cm of remnant small intestine and receive an amount of parenteral nutrition each week.

The patient may have at least about 10% (as compared to a normal healthy individual) endogenous GLP-2 levels in the fed state. The patient may have at least 15% (as compared to a normal healthy individual) endogenous GLP-2 levels in the fed state. The patient may have at least about 20% (as compared to a normal healthy individual) endogenous GLP-2 levels in the fed state. The patient may have at least about 25% (as compared to a normal healthy individual) endogenous GLP-2 levels in the fed state. The patient may have at least about 30% (as compared to a normal healthy individual) endogenous GLP-2 levels in the fed state. The patient may have at least about 35% (as compared to a normal healthy individual) endogenous GLP-2 levels in the fed state. The patient may have at least about 40% (as compared to a normal healthy individual) endogenous GLP-2 levels in the fed state. The patient may have at least about 45% (as compared to a normal healthy individual) endogenous GLP-2 levels in the fed state. The patient may have at least about 50% (as compared to a normal healthy individual) endogenous GLP-2 levels in the fed state. The patient may have at least about 55% (as compared to a normal healthy individual) endogenous GLP-2 levels in the fed state. The patient may have at least about 60% (as compared to a normal healthy individual) endogenous GLP-2 levels in the fed state. The patient may have at least about 65% (as compared to a normal healthy individual) endogenous GLP-2 levels in the fed state. The patient may have at least about 70% (as compared to a normal healthy individual) endogenous GLP-2 levels in the fed state. The patient may have at least about 75% (as compared to a normal healthy individual) endogenous GLP-2 levels in the fed state. The patient may have at least about 80% (as compared to a normal healthy individual) endogenous GLP-2 levels in the fed state. The patient may have at least about 90% (as compared to a normal healthy individual) endogenous GLP-2 levels in the fed state.

The patient may produce at least about 10 pmol/L of endogenous GLP-2 levels in the fed state. The patient may produce at least about 15 pmol/L of endogenous GLP-2 levels in the fed state. The patient may produce at least about 20 pmol/L of endogenous GLP-2 levels in the fed state. The patient may produce at least about 25 pmol/L of endogenous GLP-2 levels in the fed state. The patient may produce at least about 30 pmol/L of endogenous GLP-2 levels in the fed state. The patient may produce at least about 35 pmol/L of endogenous GLP-2 levels in the fed state. The patient may produce at least about 40 pmol/L of endogenous GLP-2 levels in the fed state. The patient may produce at least about 45 pmol/L of endogenous GLP-2 levels in the fed state. The patient may produce at least about 50 pmol/L of endogenous GLP-2 levels in the fed state. The patient may produce at least about 55 pmol/L of endogenous GLP-2 levels in the fed state. The patient may produce at least about 60 pmol/L of endogenous GLP-2 levels in the fed state. The patient may produce at least about 65 pmol/L of endogenous GLP-2 levels in the fed state. The patient may produce at least about 70 pmol/L of endogenous GLP-2 levels in the fed state.

The h(Gly2)GLP-2 may be administered at a daily dose of from 5 to 500 µg/kg. The h(Gly2)GLP-2 may be administered at a daily dose of from 30 to 150 µg/kg. The h(Gly2)GLP-2 may be administered intravenously at a daily dose of 0.04 to 0.06 mg/kg body weight, e.g., 0.05 mg/kg body weight.

The GLP-2 peptibody may be administered at a daily dosage of between 0.02 to 3.0 mg/kg, 0.02 to 0.5 mg/kg, 0.04 to 0.45 mg/kg, 0.08 to 0.4 mg/kg, 0.10 to 0.35 mg/kg, 0.20 to 0.30 mg/kg, 0.02 to 0.05 mg/kg, 0.03 to 0.04 mg/kg, 0.05 to 0.10 mg/kg, 0.10 to 0.15 mg/kg, 0.2 to 0.3 mg/kg, 0.3 to 0.4 mg/kg, 0.4 to 0.5 mg/kg, 0.5 to 0.8 mg/kg, 0.7 to 1.0 mg/kg, 0.9 to 1.2 mg/kg, 1.0 to 1.5 mg/kg, 1.2 to 1.8 mg/kg, 1.5 to 2.0 mg/kg, 1.7 to 2.5 mg/kg, or 2.0 to 3.0 mg/kg. In some embodiments, the GLP-2 peptibody comprises the sequence of any of SEQ ID NOS: 2-16. In some embodiments, the GLP-2 peptibody comprises the sequence of SEQ ID NO: 4.

The h(Gly2)GLP-2 may be administered by subcutaneous injection. Administration by subcutaneous injection can be into the abdomen, thigh, or arm. Administration by subcutaneous injection may be conducted before surgery or after surgery.

h(Gly2)GLP-2 and/or the GLP-2 peptibody may be administered to the patient at least once within one month before the surgery. h(Gly2)GLP-2 or the GLP-2 analogue may be administered once as soon as 24 hours before surgery, 18 hours before surgery, 12 hours before surgery, 9 hours before surgery, 6 hours before surgery, three hours before surgery, two hours before surgery, or one hour before surgery. Multiple administrations of h(Gly2)GLP-2 or the GLP-2 analog can be undertaken every 6, 7, 8, 9, 10, 11, 12, 13, 14, 15, 16, 17, 18, 19, 20, 21, 22, 23 or 24 hours over a period of one day, two days, three days, four days, five days, six days or seven days before surgery. Before surgery, the GLP-2 peptibody may be administered once in a subcutaneous or intravenous formulation. The GLP-2 peptibody may again be administered three, four, five, six, seven, or more days after the first dose.

Administration may be undertaken 24 hours after surgery, 18 hours after surgery, 12 hours after surgery, 9 hours after surgery, 6 hours after surgery, three hours after surgery, two hours after surgery, or one hour after surgery. After surgery, h(Gly2)GLP-2 or the GLP-2 analog may be administered about every 6, 7, 8, 9, 10, 11, 12, 13, 14, 15, 16, 17, 18, 19, 20, 21, 22, 23 or 24 hours over a period of one day, two days, three days, four days, five days, six days or seven days. After surgery, the GLP-2 peptibody may be administered once in a subcutaneous or intravenous formulation. The GLP-2 peptibody may again be administered three, four, five, six, seven, or more days after the first dose.

In certain embodiments of all aspects and embodiments described herein, the patient can be an adult, a human, or an adult human.

In some embodiments, the patient receives an amount of parenteral nutrition each week. In some embodiments, the dosing regimen is effective to reduce the parenteral nutrition by volume or frequency of administration. In some embodiments, the dosing regimen is effective to increase meal-stimulated GLP-2 secretion.

GLP-2 peptibodies of the present invention can provide at least one suitable property as compared to known proteins, such as, but not limited to, at least one of increased half-life, increased activity, more specific activity, increased avidity, increased or decreased off rate, a selected or more suitable subset of activities, less immunogenicity, increased quality or duration of at least one desired therapeutic effect, less side effects, and the like.

Typically, a suitable GLP-2 peptibody, e.g., a GLP-2 peptibody comprising the amino acid sequence of SEQ ID NO: 2 or SEQ ID NO: 4, has an in vivo half-life of or greater than about 2 hours, 3 hours, 4 hours, 6 hours, 8 hours, 10 hours, 12 hours, 14 hours, 16 hours, 18 hours, 20 hours, 22 hours, 24 hours, 26 hours, 28 hours, 30 hours, 32 hours, 34 hours, 36 hours, 38 hours, 40 hours, 42 hours, 44 hours, 46 hours, or 48 hours. In some embodiments, a recombinant GLP-2 peptibody has an in vivo half-life of between 2 and 48 hours, between 2 and 44 hours, between 2 and 40 hours, between 3 and 36 hours, between 3 and 32 hours, between 3 and 28 hours, between 4 and 24 hours, between 4 and 20 hours, between 6 and 18 hours, between 6 and 15 hours, and between 6 and 12 hours.

The GLP-2 peptibodies or specified portion or variants thereof may be produced by at least one cell line, mixed cell line, immortalized cell or clonal population of immortalized and/or cultured cells. Immortalized protein producing cells can be produced using suitable methods. Preferably, the at least one GLP-2 peptibody or specified portion or variant is generated by providing nucleic acid or vectors comprising DNA derived or having a substantially similar sequence to, at least one human immunoglobulin locus that is functionally rearranged, or which can undergo functional rearrangement, and which further comprises a peptibody structure as described herein.

The GLP-2 peptibodies can bind human protein ligands with a wide range of affinities ($K_D$). In a preferred embodiment, at least one human GLP-2 peptibody of the present invention can optionally bind at least one protein ligand with high affinity. For example, at least one GLP-2 peptibody of the present invention can bind at least one protein ligand with a $K_D$ equal to or less than about $10^{-7}$ M or, more preferably, with a $K_D$ equal to or less than about 0.1-9.9 (or any range or value therein)$\times 10^{-7}$, $10^{-8}$, $10^{-9}$, $10^{-10}$, $10^{-11}$, $10^{-12}$, or $10^{-13}$M, or any range or value therein.

The affinity or avidity of a GLP-2 peptibody for at least one protein ligand can be determined experimentally using any suitable method, e.g., as used for determining antibody-antigen binding affinity or avidity. (See, for example, Kuby, Janis *Immunology*, W. H. Freeman and Company: New York, N.Y. (1992)). The measured affinity of a particular GLP-2 peptibody-ligand interaction can vary if measured under different conditions, e.g., salt concentration and pH. Thus, measurements of affinity and other ligand-binding parameters (e.g., $K_D$, $K_a$, $K_d$) are preferably made with standardized solutions of GLP-2 peptibody and ligand, and a standardized buffer, such as the buffer described herein or known in the art.

There may or may not be a lysine (K) at the C-terminus. At the same time, in any of the embodiments or aspects described herein, lysine can be added to C-terminus. In any embodiment or aspect described herein, the GLP-2 peptibody is processed from a GLP-2 precursor polypeptide that comprises a signal peptide directly linked with GLP-2, with a linker between GLP-2 and an Fc region of any of IgG1, IgG2, IgG3 and IgG4. The Fc region may be IgG1 with the LALA mutation. The GLP-2 precursor polypeptide may have the following formula:

Signal peptide-GLP-2[A2G]-linker-IgG1(LALA)

LALA refers to the L234A and L235A (EU numbering) mutations in an antibody. The LALA mutations can greatly reduce binding to Fc gamma-Rs and in turn prevent the GLP-2 peptibodies from causing unwanted antibody effector functions. See Leabman, M. K. et al., "Effects of altered Fc gammaR binding on antibody pharmacokinetics in cynomolgus monkeys" mAbs 5(6):2013.

GLP-2 peptibodies may comprise GLP-2 fused to an Fc domain. It is contemplated that improved binding between Fc domain and the FcRn receptor results in prolonged serum half-life. Thus, in some embodiments, a suitable Fc domain comprises one or more amino acid mutations that lead to improved binding to FcRn. Various mutations within the Fc domain that effect improved binding to FcRn are known in the art and can be adapted to practice the present invention. In some embodiments, a suitable Fc domain comprises one or more mutations at one or more positions corresponding to Thr 250, Met 252, Ser 254, Thr 256, Thr 307, Glu 380, Met 428, His 433, and/or Asn 434 of human IgG1.

A GLP-2 peptibody, or specified portion or variant thereof, that partially or preferably substantially provides at least one GLP-2 biological activity, can bind the GLP-2 ligand and thereby provide at least one activity that is otherwise mediated through the binding of GLP-2 to at least one ligand, such as a GLP-2 receptor, or through other protein-dependent or mediated mechanisms. As used herein, the term "GLP-2 peptibody activity" refers to a GLP-2 peptibody that can modulate or cause at least one GLP-2 dependent activity by about 20-10,000% as compared to wildtype GLP-2 peptide or a GLP-2[A2G] peptide, preferably by at least about 60, 70, 80, 90, 91, 92, 93, 94, 95, 96, 97, 98, 99, 100, 110, 120, 130, 140, 150, 160, 170, 180, 190, 200, 250, 300, 350, 400, 450, 500, 550, 600, 700, 800, 900, 1000, 2000, 3000, 4000, 5000, 6000, 7000, 8000, 9000% or more as compared to a wildtype GLP-2 peptide or a GLP-2[A2G] peptide, depending on the assay.

The capacity of a GLP-2 peptibody or specified portion or variant to provide at least one protein-dependent activity is preferably assessed by at least one suitable protein biological assay, as described herein and/or as known in the art. A human GLP-2 peptibody or specified portion or variant of the invention can be similar to any class (IgG, IgA, IgM, etc.) or isotype and can comprise at least a portion of a kappa or lambda light chain. In one embodiment, the human GLP-2 peptibody or specified portion or variant comprises IgG heavy chain CH2 and CH3 of, at least one of subclass, e.g., IgG1, IgG2, IgG3 or IgG4.

At least one GLP-2 peptibody or specified portion or variant of the invention binds at least one ligand, subunit, fragment, portion or any combination thereof. The at least one GLP-2 peptide, variant or derivative of at least one GLP-2 peptibody, specified portion or variant of the present invention can optionally bind at least one specified epitope of the ligand. The binding epitope can comprise any combination of at least one amino acid sequence of at least 1-3 amino acids to the entire specified portion of contiguous amino acids of the sequences of a protein ligand, such as a GLP-2 receptor or portion thereof.

The invention also relates to peptibodies, ligand-binding fragments and immunoglobulin chains comprising amino acids in a sequence that is substantially the same as an amino acid sequence described herein. Preferably, such peptibodies or ligand-binding fragments thereof can bind human GLP-2 ligands, such as receptors, with high affinity (e.g., $K_D$ less than or equal to about $10^{-7}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

As those of skill will appreciate, the present invention includes at least one biologically active GLP-2 peptibody or specified portion or variant of the present invention. In some embodiments, biologically active GLP-2 peptibodies or specified portions or variants have a specific activity at least 2%, 3%, 4%, 5%, 6%, 7%, 8%, 9%, 10%, 12%, or 15%, of that of the native (non-synthetic), endogenous or related and known inserted or fused protein or specified portion or variant.

The manner of preparing GLP-2 peptibodies is described in U.S. Provisional Application No. 62/548,601, filed Aug. 22, 2017. Further, any of the modifications described in Application No. 62/548,601 may be made to the above-described GLP-2 peptibodies.

In some embodiments, the dosing regimen is effective to increase wet weight absorption compared to a baseline wet weight absorption by said patient. Such patient may have short bowel syndrome with Crohn's disease, or secondary to Crohn's disease. Such patient may have short bowel syndrome with mesenteric infarction, or secondary to mesenteric infarction. Such patient may have short bowel syndrome with volvulus, or secondary to volvulus. Such patient may have short bowel syndrome with congenital intestinal abnormalities, or secondary to congenital intestinal abnormalities. Such patient may have short bowel syndrome with, or secondary to, multiple strictures due to adhesions or radiation. Such patient may have short bowel syndrome with, or secondary to, vascular ischemia. The patient may have limited, but some detectable, meal-stimulated GLP-2 secretion (as compared to a normal healthy individual). The patient may have less, but some detectable, GLP-2 producing tissue (as compared to a normal healthy individual). The patient may have elevated basal levels of endogenous GLP-2 (as compared to a normal healthy individual).

In some embodiments, the dosing regimen is effective to enhance intestinal absorption by the patient. Such patient may have short bowel syndrome with Crohn's disease, or secondary to Crohn's disease. Such patient may have short bowel syndrome with mesenteric infarction, or secondary to mesenteric infarction. Such patient may have short bowel syndrome with volvulus, or secondary to volvulus. Such patient may have short bowel syndrome with congenital intestinal abnormalities, or secondary to congenital intestinal abnormalities. Such patient may have short bowel syndrome with, or secondary to, multiple strictures due to adhesions or radiation. Such patient may have short bowel syndrome with, or secondary to, vascular ischemia. The patient may have limited, but some detectable, meal-stimulated GLP-2 secretion (as compared to a normal healthy individual). The patient may have less, but some detectable, GLP-2 producing tissue (as compared to a normal healthy individual). The patient may have elevated basal levels of endogenous GLP-2 (as compared to a normal healthy individual).

In some embodiments, the dosing regimen is effective to decrease the fecal wet weight of said patient. Such patient may have short bowel syndrome with Crohn's disease, or secondary to Crohn's disease. Such patient may have short bowel syndrome with mesenteric infarction, or secondary to mesenteric infarction. Such patient may have short bowel syndrome with volvulus, or secondary to volvulus. Such patient may have short bowel syndrome with congenital intestinal abnormalities, or secondary to congenital intestinal abnormalities. Such patient may have short bowel syndrome with, or secondary to, multiple strictures due to adhesions or radiation. Such patient may have short bowel syndrome with, or secondary to, vascular ischemia. The patient may have limited, but some detectable, meal-stimulated GLP-2 secretion (as compared to a normal healthy individual). The patient may have less, but some detectable, GLP-2 producing tissue (as compared to a normal healthy individual). The patient may have elevated basal levels of endogenous GLP-2 (as compared to a normal healthy individual).

In some embodiments, the dosing regimen is effective to increase the urine weight of said patient. Such patient may have short bowel syndrome with Crohn's disease, or secondary to Crohn's disease. Such patient may have short bowel syndrome with mesenteric infarction, or secondary to mesenteric infarction. Such patient may have short bowel syndrome with volvulus, or secondary to volvulus. Such patient may have short bowel syndrome with congenital intestinal abnormalities, or secondary to congenital intestinal abnormalities. Such patient may have short bowel syndrome with, or secondary to, multiple strictures due to adhesions or radiation. Such patient may have short bowel syndrome with, or secondary to, vascular ischemia. The patient may have limited, but some detectable, meal-stimulated GLP-2 secretion (as compared to a normal healthy individual). The patient may have less, but some detectable, GLP-2 producing tissue (as compared to a normal healthy individual). The patient may have elevated basal levels of endogenous GLP-2 (as compared to a normal healthy individual). In some embodiments, the urine weight is increased by at least 5% as compared to urine weight of said patient before said dosing regimen. In some embodiments, the urine weight is increased by at least 10% as compared to urine weight of said patient before said dosing regimen.

In some embodiments, the patient having short bowel syndrome has reduced crypt depth as compared to a normal healthy individual and the dosing regimen is effective to increase the crypt depth in the patient. The crypt depth may be in the small intestine. See, e.g., FIGS. 1-3 in which administration of GLP-2 peptibody B264, GLP-2 peptibody K274 or h(Gly2)GLP-2 increased crypt depth in the small intestine after administration.

In some embodiments, the patient having short bowel syndrome has reduced mitotic figures per 100 crypt epithelial cells as compared to a normal healthy individual, and the dosing regimen is effective to increase the number of mitotic figures per 100 crypt epithelial cells of the patient.

In some embodiments, the regimen involves administration of h(Gly2)GLP-2 over a period of at least 21 days. The period may be at least 25 days, at least 30 days, at least 35 days, at least 40 days, at least 45 days, at least 50 days, at least 55 days, at least 60 days, or at least 65 days.

In some embodiments, the patient is an adult and the h(Gly2)GLP-2 is administered intravenously at a daily dose of 0.04 to 0.06 mg/kg body weight, e.g., 0.05 mg/kg body weight.

In some embodiments, the dosing regimen is effective to restore at least a portion of, or to enhance, the ileal brake mechanism of the patient. In some embodiments, the dosing regimen is effective to reduce gastric hypersecretion in the patient with short bowel syndrome. In some embodiments, the dosing regimen is effective to reduce or suppress gastric secretion in the patient with short bowel syndrome. In some embodiments, the dosing regimen is effective to reduce the speed of gastric emptying in a patient with short bowel syndrome. The patient may have rapid gastric emptying. In some embodiments, the dosing regimen is effective to induce small intestine growth in the patient with short bowel syndrome.

In some embodiments, the dosing regimen is effective to upregulate protein transport in the patient with short bowel syndrome. The protein transport may be across the small intestine, such as across the villus, across the crypt, or across both the villus and crypt.

In some embodiments, the dosing regimen is effective to reduce the likelihood of dehydration recurrence in the patient with short bowel syndrome. In some embodiments, the dosing regimen is effective to reduce the likelihood of renal insufficiency recurrence in the patient with short bowel syndrome. In some embodiments, the dosing regimen is effective to reduce the recurrence of kidney stones in the patient with short bowel syndrome. In some embodiments, the dosing regimen is effective to enhance intestinal absorption by the patient with short bowel syndrome. In some embodiments, the dosing regimen is effective to reduce the dependency on parenteral nutrition by the patient.

In some embodiments, the dosing regimen is effective to increase the villus height (in small intestine) of said patient. Villus height and crypt depth may be measured using light microscopy (eyepiece micrometer) as the mean of ten well-oriented villi and crypts. The number of mitotic figures per 100 crypt epithelial cells can also be calculated.

In some embodiments, the dosing regimen is effective to increase the crypt depth (in small intestine) of said patient.

EXAMPLES

The present invention is also described and demonstrated by way of the following examples. However, the use of these and other examples anywhere in the specification is illustrative only and in no way limits the scope and meaning of the invention or any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Histology Study of Villi Length and Crypt Depth in GLP-2 Peptibody B264

Various doses of GLP-2 peptibody B264 were analyzed to assess the pharmacodynamic plateau, with the primary endpoint a measurement of the small intestinal weight relative to the total body weight and a histology study of the length of villi. 11 groups of six female CD-1 mice each were formed. The groups are summarized in Table 1 below.

TABLE 1

| Group | Test agent | Dose (mg/kg) | Dose Regimen | Study Duration |
|---|---|---|---|---|
| 1 | Vehicle 1 | 0 | BID, 14 days | 15 days |
| 2 | GLP-2[A2G] | 0.025 | Q3D, 14 days | 15 days |
| 3 | GLP-2[A2G] | 0.25 | Q3D, 14 days | 15 days |
| 4 | Vehicle 2 | 0 | Q3D, 14 days | 15 days |
| 5 | Vehicle 2 | 0 | Q3D, 14 days | 21 days |
| 6 | GLP-2 peptibody B264 | 0.45 | Q3D | 15 days |
| 7 | GLP-2 peptibody B264 | 1.5 | Q3D over 14 days | 15 days |
| 8 | GLP-2 peptibody B264 | 4.5 | Q3D over 14 days | 15 days |
| 9 | GLP-2 peptibody B264 | 15 | Q3D over 14 days | 15 days |

TABLE 1-continued

| Group | Test agent | Dose (mg/kg) | Dose Regimen | Study Duration |
|---|---|---|---|---|
| 10 | GLP-2 peptibody B264 | 4.5 | Q3D over 14 days | 18 days |
| 11 | GLP-2 peptibody B264 | 4.5 | Q3D over 14 days | 21 days |

Figure 4:
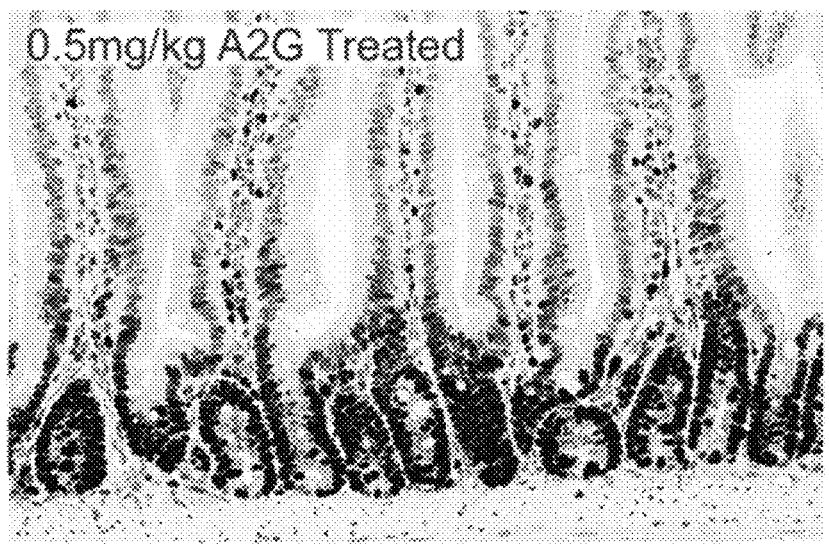
FIG. 4 shows the results of a histology study of localization of GLP-2[A2G], an h(Gly2)GLP-2, to the crypts and villi of the small intestine.
Figure 5A:
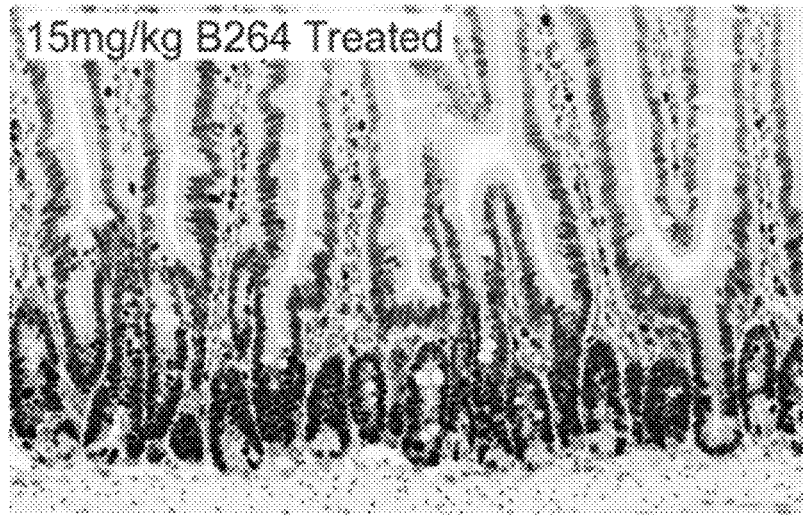
FIGS. 5A and 5B show the results of a histology study of localization of GLP-2 peptibody B264 (5A) and GLP-2 peptibody K274 (5B) to the crypts and villi of the small intestine.
Figure 5B:

For histology, four micron paraffin sections were prepared for H&E and Ki67 IHC staining. After whole slide scanning, an imagescope was used to measure villi length and crypt depth, and to analyze Ki67. The antibody against Ki67 is a rabbit antibody sold by Adcam®, catalog number ab 616667. The antibody was used at a working concentration of 1:100 and was detected using a Leica® Refine Kit. The Ki67 staining results are shown in FIGS. 4, 5A and 5B. There is strong localization of GLP-2 peptibody B264, GLP-2 peptibody K274, and a GLP-2[A2G] peptide to the villi and crypt cells. See, e.g., Example 13 of U.S. Provisional Application No. 62/548,601, filed Aug. 22, 2017 for more data and examples with respect to GLP-2 peptibody B264, GLP-2 peptibody K274, and a GLP-2[A2G] peptide.

Example 2: Administration of a GLP-2 Peptibody to a Patient Before Surgery

A patient with Crohn's disease is scheduled to undergo surgery for small intestine resection in one month. The patient is expected to have a small intestine of 150 cm length after the surgery. The small intestine is expected to remain in continuity with the colon. The patient is expected to develop a mild case of short bowel syndrome and need parenteral nutrition support. As part of a treatment plan to reduce inflammation after surgery, an issue with Crohn's disease, and to minimize the need for parenteral nutrition support, a GLP-2 peptibody will be administered subcutaneously to the patient each week at a dose of about 1.4 mg/kg. The patient will be monitored for any side effects relating to digestion and intestinal absorption.

Example 3: Administration of a Teduglutide to a Patient Before Surgery

A patient with Crohn's disease is scheduled to undergo surgery for small intestine resection in one month. The patient is expected to have a small intestine of 150 cm length after the surgery. The small intestine is expected to remain in continuity with the colon. The patient is expected to develop a mild case of short bowel syndrome and need parenteral nutrition support. As part of a treatment plan to reduce inflammation after surgery, an issue with Crohn's disease, and to minimize the need for parenteral nutrition support, 0.05 mg/kg h(Gly2)GLP-2 will be administered intravenously to the patient each day. The patient will be monitored for any side effects relating to digestion and intestinal absorption.

Example 4: Administration of a GLP-2 Peptibody to a Patient During and after Surgery A patient with volvulus is undergoing surgery for small intestine resection. The patient is expected to have a small intestine of 100 cm length after the surgery. The small intestine is expected to remain in continuity with the colon after the surgery. The patient is expected to develop short bowel syndrome and need parenteral nutrition support. As part of a treatment plan to reduce inflammation from the surgery and to minimize the need for parenteral nutrition support, h(Gly2)GLP-2 is administered intravenously to the patient during the surgery. The daily dose administered is 0.05 mg/kg body weight. After the surgery, h(Gly2)GLP-2 will be administered intravenously at a daily dose of 0.05 mg/kg body weight. The patient will be monitored to determine if parenteral nutrition support can be reduced or withdrawn.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

Patents, patent applications, publications, product descriptions, and protocols are cited throughout this application, the disclosures of which are incorporated herein by reference in their entireties for all purposes.

The invention claimed is:

1. A method of treating a patient who has undergone surgery and has short bowel syndrome comprising administering a GLP-2 peptibody to the patient within a period of 48 hours after surgery, wherein the GLP-2 peptibody comprises one of the sequences set forth in SEQ ID NO: 2-16.

2. The method of claim 1, wherein the GLP-2 peptibody comprises the sequence set forth in SEQ ID NO: 2 or SEQ ID NO: 4.

3. The method of claim 1, wherein the GLP-2 peptibody is administered subcutaneously to the patient at a dose of about 1.4 mg/kg.

4. The method of claim 3, wherein the GLP-2 peptibody is administered to the patient within a period of 12 hours after surgery.

5. The method of claim 1, wherein the patient is receiving parenteral nutrition.

6. The method of claim 5, wherein the patient receives an amount of parenteral nutrition each week and the method is effective to reduce the amount of parenteral nutrition received by the patient.

7. The method of claim 1, wherein the patient has short bowel syndrome secondary to one or more of Crohn's disease, mesenteric infarction, volvulus, multiple strictures due to adhesions or radiation, vascular ischemia.

8. The method of claim 1, wherein the patient has one or more of
   a) limited, but some detectable, meal-stimulated GLP-2 secretion (as compared to a normal healthy individual,
   b) less, but some detectable, GLP-2 producing tissue (as compared to a normal healthy individual, and
   c) elevated basal levels of endogenous GLP-2 (as compared to a normal healthy individual.

* * * * *